(12) United States Patent
Fromherz et al.

(10) Patent No.: US 7,611,863 B2
(45) Date of Patent: Nov. 3, 2009

(54) SELECTIVE STAINING OF BIOMEMBRANES USING VOLTAGE-SENSITIVE DYES

(75) Inventors: Peter Fromherz, Munich (DE); Gerd Huebener, Munich (DE); Marlon J. Hinner, Munich (DE)

(73) Assignee: Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 33 days.

(21) Appl. No.: 11/030,313

(22) Filed: Jan. 7, 2005

(65) Prior Publication Data
US 2005/0260698 A1    Nov. 24, 2005

(30) Foreign Application Priority Data
Jan. 8, 2004    (EP)    ................... 04000268
Oct. 19, 2004   (EP)    ................... 04024877

(51) Int. Cl.
*G01N 1/30*    (2006.01)
(52) U.S. Cl. ............................. 435/40.5; 435/4; 435/7.2; 436/111
(58) Field of Classification Search ................. 435/40.5
See application file for complete search history.

(56) References Cited
U.S. PATENT DOCUMENTS
4,723,020 A    2/1988    Hugl et al.
5,316,906 A *  5/1994    Haugland et al. .............. 435/4
2003/0215951 A1  11/2003  Law et al.

FOREIGN PATENT DOCUMENTS
DE    3346795 A1    7/1985
WO    WO 92/02632 A1    2/1992
WO    WO 02/08454 A3    1/2002
WO    WO 03/047499 A2    6/2003
WO    WO 03/047499 A3    6/2003

OTHER PUBLICATIONS

Baker et al, UBEP 1999 Abstracts http://lifesciences.asu.edu/ubep99/abstracts/abst63/index.html.*
Hassner, A. et al. "Charge-Shift Probes of Membrane Potential. Synthesis," J. of Organic Chemistry, vol. 49, No. 14, 1984, pp. 2546-2551.
Fluhler, E. et al. "Spectra, Membrane Binding, and Potentiometric Responses of New Charge Shift Probes," Biochemistry, vol. 24, No. 21, 1985, pp. 5749-5755.
Fedosova, N. U. et al. "Fluorescent Styryl Dyes as Probes for Na,K-ATPase Reaction Mechanism: Significance of the Charge of the Hydrophilic Moiety of RH Dyes," Biochemistry, vol. 34, No. 51, 1995, pp. 16806-16814.

* cited by examiner

*Primary Examiner*—Jon P Weber
*Assistant Examiner*—Tiffany M Gough
(74) *Attorney, Agent, or Firm*—Rothwell, Figg, Ernst & Manbeck, P.C.

(57) ABSTRACT

The present invention relates to a method for staining membranes, in particular, a method for selective staining of cells using voltage-sensitive dyes.

10 Claims, 17 Drawing Sheets

Figures and Captions

Figure 1:
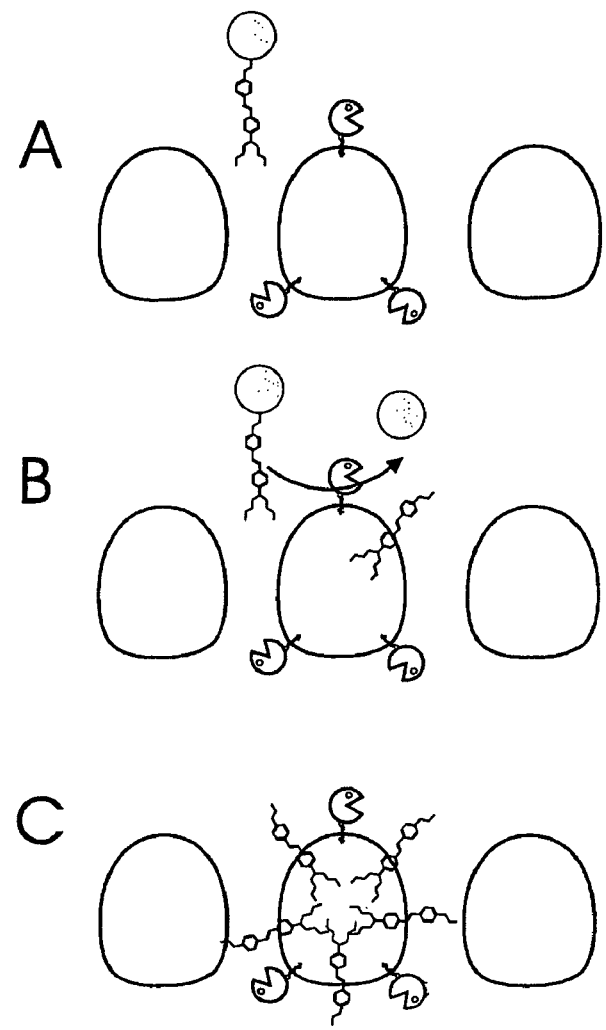

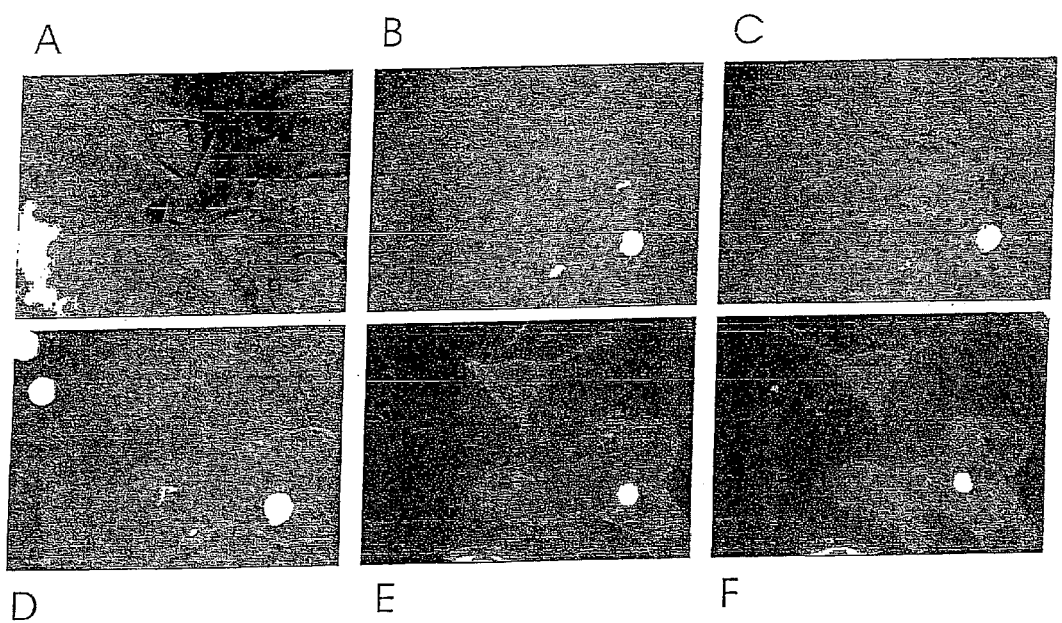
Fig. 12A to F

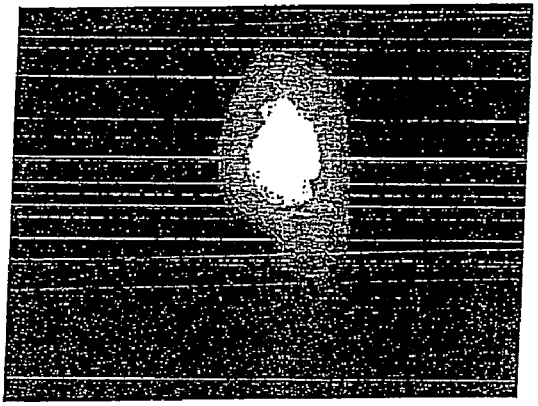
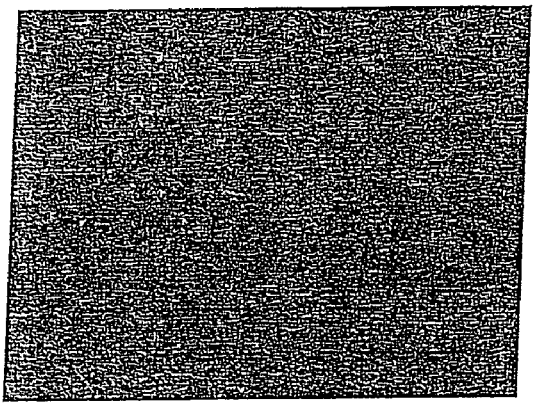
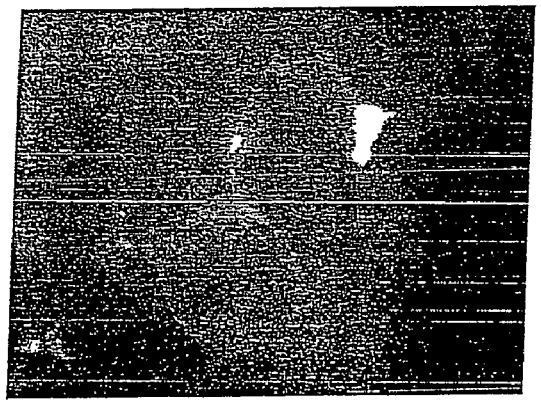
Fig. 13 A to C

SEQUENCE LISTING

```
<160> NUMBER OF SEQ ID NOS: 2

<210> SEQ ID NO 1
<211> LENGTH: 80
<212> TYPE: PRT
<213> ORGANISM: Artificial Sequence
<220> FEATURE:
<223> OTHER INFORMATION: plasma membrane anchor containing regions from
      eukaryotic c-myc protein, a bacterial cloning site and influenza
      hemagglutinin

<400> SEQUENCE: 1

Met Gly His His His His His His Tyr Pro Tyr Asp Val Pro Asp Tyr
1               5                   10                  15

Ala Gly Gly Lys Lys Lys Lys Leu Leu Leu Leu Leu Leu Leu Leu Leu
                20                  25                  30

Leu Leu Leu Leu Leu Leu Leu Leu Leu Leu Leu Leu Leu Val Gln Gln
            35                  40                  45

Gln Asp Tyr Asp Ile Pro Thr Thr Ala Ser Arg Gly Gln Ala Arg Ala
    50                  55                  60

Asp Pro Glu Phe Asp Ile Glu Gln Lys Leu Ile Ser Glu Glu Asp Leu
65                  70                  75                  80

<210> SEQ ID NO 2
<211> LENGTH: 4
<212> TYPE: PRT
<213> ORGANISM: Artificial Sequence
<220> FEATURE:
<223> OTHER INFORMATION: plasma membrane anchor containing regions from
      eukaryotic c-myc protein, a bacterial cloning site and influenza
      hemagglutinin

<400> SEQUENCE: 2

Val Gln Gln Gln
1
```

SELECTIVE STAINING OF BIOMEMBRANES USING VOLTAGE-SENSITIVE DYES

The present invention relates to a method for enzyme activation of amphiphiles. The method can be used for staining membranes, in particular, for selective staining of cells using voltage-sensitive dyes.

Voltage-sensitive fluorescent dyes are well established probes for optical recording of voltage transients in nerve membranes. Since their first application in 1968[1] and their further development in the following decades[2-10], they have been successfully used in cultured nerve cells and in nerve tissue[11-13]. Optical recording allows the study of neurons and brain at a high temporal and spatial resolution. However, voltage-sensitive dyes suffer from various limitations such as pharmacological side effects, phototoxicity, sensitivity, photoinstability and unselective staining.

Common extracellular application of voltage-sensitive dyes leads to staining of all cells in a tissue. As a consequence, voltage transients of individual neurons cannot be measured. Significant progress would be achieved if a satisfactory method for selective staining of individual neurons or groups of neurons were available. So far, intracellular application of dyes has been considered[14-15]. With this method, however, also intracellular structures are stained with the concomitant effects of background fluorescence and phototoxicity. In addition, slow intracellular diffusion may lead to incomplete staining. Attempts using genetically encoded fluorescent proteins with intrinsic voltage sensitivity had modest success hitherto[16,17].

Further, selective activation of amphiphiles and, in particular, selective binding of activated amphiphiles to certain membranes is of great interest. For example, selective labelling of cancer cells would be of great benefit.

Therefore, it was an object of the invention to provide a method for selective activation of amphiphiles and, in particular, a method for staining membranes eliminating, at least partly, the drawbacks of the prior art.

According to the invention, this object is achieved by a method for enzymatic activation of an amphiphile comprising (a) providing an amphiphile precursor which contains an enzymatically cleavable group, and (b) cleaving the amphiphile precursor using an enzyme, thereby forming the amphiphile. The invention, in particular, relates to a method for staining membranes comprising the steps: (i) providing a dye precursor which contains an enzymatically cleavable group; (ii) cleaving of the dye precursor using an enzyme, thereby forming the dye, and (iii) binding of the dye to the membrane.

The invention, in particular, relates to enzyme-induced staining of cell membranes by fluorescent voltage-sensitive dyes. The approach relies on the induction of membrane binding by enzymatic conversion of a water soluble precursor dye. We synthetized an amphiphilic hemicyanine dye with and without an additional phosphate appendix at its polar headgroup. The fluorescence of these dyes is negligible in water but high when bound to lipid membranes. By fluorescence titration with lipid vesicles it was shown that the phosphate group lowers the partition coefficient from water to membrane by more than an order of magnitude. By isothermal titration calorimetry, we showed that the dye phosphate was a substrate for a water soluble alkaline phosphatase following Michaelis-Menten kinetics. In a suspension of lipid vesicles, the enzyme reaction led to a fluorescence increase due to enhanced membrane binding of the product dye in accord with the Michaelis-Menten kinetics of the reaction and the partition coefficients of substrate and product. We successfully tested the staining method by fluorescence microscopy with individual giant lipid vesicles and with individual red blood cells. In both systems, the membrane fluorescence due to bound hemicyanine was enhanced by an order of magnitude, proving the feasibility of enzyme induced staining with voltage-sensitive dyes.

More particularly, the present invention relates to a novel approach to the selective staining of cells in tissue with so-called Fast Voltage Sensitive Dyes. These dyes are membrane-bound, optical probes of membrane potential. The invention relies on the activation of binding to a cell membrane by enzymatic action of a preferably membrane-bound enzyme. Since the dye can probe the membrane potential only when it is bound, activation of binding is coincident with the activation of voltage sensitivity. To that end, especially weakly binding precursor dyes were designed and synthesized, in particular, precursor dyes containing additional phosphate appendices at the lipophilic tail of the dyes. These dyes are membrane-impermeable and water-soluble. The idea that the binding of amphiphiles to lipid membranes can be activated by enzymatic hydrolysis has not been described before. Herein the principal feasibility of the approach to the successful implementation of selective staining on cultured mammalian cells with a voltage-sensitive dye has been demonstrated. Fast Voltage Sensitive Dyes exhibit a temporal and spatial resolution that is, at least in combination, not attainable with present day techniques. The inventive method of selective staining with Fast Voltage Sensitive Dyes allows previously impossible insights into the function of neuronal networks.

The present invention provides a new concept for selective incorporation of amphiphiles into membranes and, in particular, for selective staining of membranes and cells with voltage sensitive dyes. The underlying principle is to increase the binding strength of the amphiphile, e.g. dye, to membranes by enzymatic cleavage of a functional group that impairs binding. The work presented provides the physicochemical fundament for that mechanism. In addition, it implies a method for screening dyes, functional groups and enzymes. The issues considered are (i) a development of amphiphile, e.g. dye pairs with a large difference of resolvation energies upon membrane binding, (ii) an application of voltage-sensitive chromphores that do not permeate a cell membrane such as ANNINE dyes[9,10], and (iii) the transfection of eucaryotic cells with membrane-bound enzymes suitable for dye hydrolysis.

The present invention relates to a method for enzyme activation of an amphiphile and, in particular, to a method for staining membranes, in particular, lipid membranes. The method includes application of a precursor and its local activation by an enzyme, in particular, its local activation at a selected cell by a genetically encoded enzyme. The activation can comprise e.g. an induction of interaction with a membrane, an induction of fluorescence quantum yield or an induction of voltage sensitivity.

In a first step, an amphiphile precursor, in particular, a dye precursor is provided. This precursor is characterized by two specific features, namely 1) it contains an enzymatically cleavable group and 2) this group impairs binding of the precursor to membranes. Preferably, the enzymatically cleavable groups are hydrophilic groups preventing or, at least, impeding binding of the precursor to membranes.

In a next step, the amphiphile precursor, in particular, the dye precursor is cleaved using an enzyme. Thereby the enzymatically cleavable group is split off and the actual amphiphile, e.g. a dye, is formed. Especially preferably, one or more hydrophilic groups are split off. By splitting off hydrophilic groups the actual amphiphile, e.g. a dye, is formed which then can bind to the membrane. According to the invention, selective incorporation of the amphiphile into a particular membrane, e.g. dyeing of particular membranes takes place only in the presence of the corresponding enzyme belonging to the cleavable group. Thus, particular membranes, e.g. membranes of individual and specific cells can be marked or dyed selectively. In particular, the enzymatically cleavable group is selected in such a way that the target cell contains or expresses the respective enzyme. For example, phosphate-modified amphiphiles may be hydrolyzed by alkaline phosphatase from the human placenta (PLAP).

In an especially preferred embodiment, the membrane is a biomembrane, in particular, a naturally occurring biomembrane, e.g. a cell wall. Especially preferably, it is the cell wall of a nerve cell or a cancer cell. Surprisingly, it has been found that natural membranes can be dyed by the method of the invention. This could not readily be expected due to the normally readily occurring binding of dyes to proteins present in cell membranes and due to the fact that cell membranes exhibit a microenvironment that is quite different from that of an artificial membrane, e.g. due to the charged lipids. Thus, voltage-sensitive fluorescent dyes are powerful probes for directly studying neuronal processes.

Dyeing according to the invention can be effected by all dyes allowing detection due to their color or their color change. Preferably, a voltage-sensitive dye is used and, more preferably, a voltage-sensitive fluorescent dye, in particular, for dyeing nerve cells. Dyeing nerve cells with such dyes allows measurement of voltage transients of individual neurons. Particularly preferred are amphiphilic dyes.

Especially good results were obtained with dye precursors of the formula (I)

$$X\text{-}A\text{-}ZR^1R^2$$

in particular, of the formula (I')

$$X\text{-}A\text{-}NR^1R^2$$

wherein A denotes a voltage-sensitive chromophore which optionally can contain one or more groups Q selected from $-(CH_2)_m-SO_2OH$, $-(CH_2)_m-N^+(CH_3)_3$, $-CH_2-CHOH-CH_2-N^+(CH_3)_2-CH_2-CH_2-OH$, $-OH$, $-O-PO(OH)_2$, $-O-SO_2OH$, $-(CH_2)_n-OH$, $-(CH_2)_n-O-PO(OH)_2$, $-(CH_2)_n-O-SO_2OH$, an N- or O-linked (poly)carbohydrate and/or an N- or O-linked (poly) amino acid, m and n independently represent an integer from 0 to 20, in particular, from 1 to 5, X denotes a polar head group selected from $-(CH_2)_m-SO_2OH$, $-(CH_2)_m-N^+(CH_3)_3$, $-CH_2-CHOH-CH_2-N^+(CH_3)_2-CH_2-CH_2-OH$ or X represents a group $-R^3-Y$ or a group Y, wherein $R^3$ is a hydrocarbon linking group with 1-20 C atoms, preferably $-(CH_2)_m-$ with m=1-20, in particular, 1-5, and wherein Y is selected from $-OH$, $-O-PO(OH)_2$, $-O-SO_2OH$, a diphosphate group, a (poly)carbohydrate and/or a (poly)amino acid, Z denotes a group 15 element selected from N, P, As, Sb or Bi, preferably, N, and $R^1$ and $R^2$ independently at each occurrence represent a $C_1$-$C_{20}$ hydrocarbon residue which can be substituted by one or more groups Y, with the proviso that the dye precursor contains at least one group Y.

Especially preferably, A is selected from

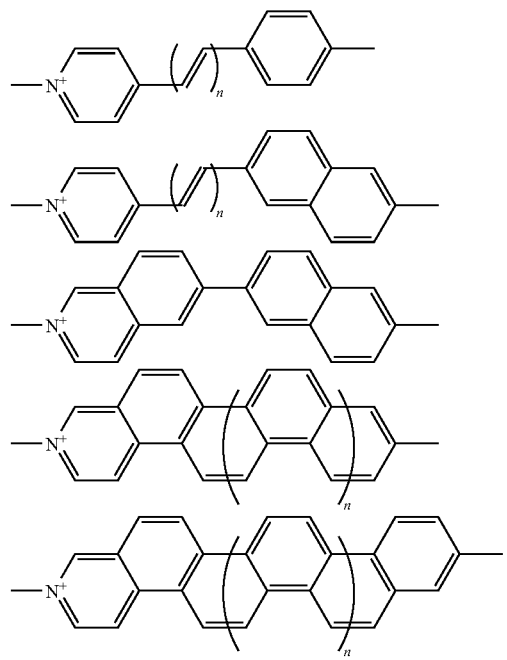

wherein n is an integer from 0-5 each, more preferably from 0-2 each. A polar head group is present at this chromophore (namely X, on the left side) as well as an amine group (namely $NR^1R^2$ on the right side).

In a preferred embodiment of the present invention, the head group known for these dyes is replaced by a group being or comprising a hydrophilic group Y selected from $-OH$, $-O-PO(OH)_2$, $-O-SO_2OH$, a diphosphate group, a carbohydrate and/or a (poly)amino acid. A suitable carbohydrate, for example, is beta-galactosidase, however, generally all mono-, di- or oligocarbohydrates. Phosphate is the most preferred group Y. This group can be split off e.g. with alkaline phosphatase which can be overexpressed without toxic effects.

Further it has been found that dyes containing a phosphate group show high solubility in aqueous systems, which is a prerequisite for the application in intracellular staining methods.

Through group Y the dye precursor, compared with the actual dye, is provided with a hydrophilic group which impedes or prevents binding of the dye to the membrane. Said group is then split off by an enzyme, leading to a dye capable of binding to the membrane, as described above. Further preferably, the head group is replaced by a group $-R^3-Y$, wherein Y is defined as above and $R^3$ is a hydrocarbon linking group having 1-20, in particular, 1-5 C atoms, wherein $R^3$ preferably constitutes $-(CH_2)_m-$ with m=1-20, in particular, 1-5.

Therefore, in a preferred embodiment, a dye precursor is employed which contains a polar group Y at the head group. The binding strength difference between precursor and dye, however, is only moderate. Further, the introduction of more than one polar group does not substantially increase this shift.

Each of $R^1$ and $R^2$ forming the tail group thereby is a $C_1$-$C_{20}$, especially a $C_1$-$C_{10}$ hydrocarbon group which can be linear or branched and saturated or mono- or polyunsaturated.

In a further preferred embodiment, $R^1$ and $R^2$ are a $C_{10}$-$C_{20}$, in particular, a $C_{10}$-$C_{14}$ hydrocarbon group.

In a further, particularly preferred embodiment, at least one of residues $R^1$ and/or $R^2$ contains one or more groups Y, i.e. the dye precursor is derivatized by hydrophilic groups at the hydrophobic end, compared with the dye. In the case of splitting off the hydrophilic group enhanced binding to the membrane by several magnitudes was observed. In addition, the dyes with modified hydrophobic ends that contained a $C_8$ or a longer hydrocarbon group proved to be cell membrane-impermeable, a crucial prerequisite for application of the method for cell staining.

Therefore, in a further preferred embodiment, a dye precursor is employed which contains one or more polar groups Y at the tail. The binding strength difference between precursor and dye is quite high. The precursor, e.g. a phosphorylated dye precursor, in this case is no longer an amphiphile, since both head and tail exhibit a high polarity. The difference in binding strength amounts to about four orders of magnitude.

Groups $R^1/R^2$ which are substituted by polar groups Y are particularly preferred. In experiments performed with such dyes containing $C_{10}$ and $C_{12}$ groups substituted with phosphate groups it was found that an overall high lipophilicity of the dye produced after enzymatic activation is beneficial for achieving a strong and well localized staining. Particularly preferred are Di-10-phosphato-ASPBS and Di-12-phosphato-ASPBS.

It must be emphasized that not the length of the lipophilic tail is the most important parameter. Instead, the overall lipophilicity of dye precursor and dye are crucial for the success of selective staining. The intensity of staining is a function of two competing processes: While the intensity increases with the amount of enzymatically hydrolysed precursor, it decreases by diffusion of produced dye away from the active cell. Therefore the selectivity of staining depends on:

- a sufficient difference in binding strength of precursor dye and product dye to minimize staining of the cell membranes by precursor dye
- a sufficiently large binding strength of the produced dye to ensure strong staining of the membrane. In addition, the amount of free dye in the aqueous solution directly adjacent to the membrane is minimized, which in turn reduces unselective staining originating from dye that diffuses away from the active cell
- a sufficiently high enzymatic activity of the membrane to ensure that the staining process proceeds more quickly than the diffusion process.
- limiting the reaction time to a time span where the equilibrium diffusion profile is not fully developed.

In a further preferred embodiment, a dye precursor is used which has a substituent at the voltage-sensitive chromophore A, in particular, one of the above-mentioned substituents X or Y. Thus, it is possible to provide compounds which exhibit dye activity, such as fluorescence activity, only after enzymatic cleavage and, even more preferred, voltage sensitivity only after enzymatic cleavage.

In another preferred embodiment, the dye or dye precursor, respectively, contains a group which promotes covalent binding to membranes, e.g. a reactive group such as isothiocyanate or maleimide. Such group which, in its reactive form, preferably is activated as well only by the enzymatic reaction enables further enhanced binding of the dye to the membrane. However, such a reactive binding group may also be present already in the dye precursor in its active form. Besides the Van der Waal's binding forces between the dye and the membrane occurring in the method of the invention covalent binding forces can be utilized as well.

The enzyme used for cleaving the dye precursor is preferably added to the system, e.g. a cell. Preferably, thus, an enzyme is concerned which is not naturally present in the cell but is only added, e.g. on the protein or nucleic acid level. Especially preferably, a cell is transfected with a nucleic acid section coding for the desired enzyme, thus allowing selective expression or overexpression of the enzyme by the cell to be analysed.

Particularly preferably, selective staining of cells by enzyme activation is achieved by expression of the respective enzyme in the cell of interest, e.g. with an expression system, wherein the enzyme is present on the surface of the cell. Most preferably, staining is achieved with (over)expressed bound enzyme.

In a particularly preferred embodiment, the enzyme to be expressed by a transfected cell is additionally provided with a targeting signal which directs the enzyme to the cell wall. Such a plasma membrane anchor preferably contains a plasma membrane directing domain, such as a hydrophobic alpha-helix poly-(L)-leucin section and, moreover, preferably one or more of the following sections: a cloning site for insertion of the desired enzyme, a c-myc-epitope tag for immunolocalization, a domain for direction of topology (positive-inside-rule), a HA-epitope tag for immunolocalization and/or a his tag for protein clean-up. A preferred example of such a plasma membrane anchor has the sequence: Met Gly His His His His His His Tyr Pro Tyr Asp Val Pro Asp Tyr Ala Gly Gly Lys Lys Lys Lys (Leu)$_{22}$ Val Gln Gln Gln Asp Tyr Asp Ile Pro Thr Thr Ala Ser Arg Gly Gln Ala Arg Ala Asp Pro Glu Phe Asp Ile Glu Gln Lys Leu Ile Ser Glu Glu Asp Leu. [SEQ ID NO: 1].

A plasma membrane targeting signal equipped for the facile construction of fusion proteins between membrane targeting signal and enzymes is herein provided. H is also called Artificial Plasma Membrane Anchor (ArtPlasMA). H contains a hydrophobic stretch of 22 leucine residues serving as a plasma membrane targeting signal and anchor. H is followed by the sequence Val Gln Gln Gln [SEQ ID NO: 2] which provides a clear border for the hydrophobic region. Four lysine residues precede the N-terminal side of the 22L stretch. The N-terminus is therefore cytoplasmic, making ArtPlasMA a type II membrane anchor. In addition, the construct contains three standard tags c-myc, HA and 6HIS-tag. ArtPlasMA can be used for targeting enzymes (e.g. Placental Phosphatase (PLAP)) to the plasma membrane by making fusion constructs. These fusion constructs resulting in the expression of plasma membrane anchor comprising enzymes allow for the selective provision of certain enzymes in specific cells.

Further it has been found that the Van der Waal's binding between the dye and the membrane leads to an equilibrium, i.e. the binding of the dye to the membrane is not irreversible but, rather, some dyes can also escape from the membrane. To achieve further improvement of the signal to noise ratio, preferably, a second enzyme is provided which converts free dye, i.e. dye not bound to the membrane, into the dye precursor or into a non-active form.

In a further preferred embodiment, the method of the invention is used for intracellular staining, the dye precursor being injected in the cell in this case. Using water-soluble dye precursor enables complete dyeing of the structures of interest present inside the cell due to enhanced water-solubility and diffusibility within the cell before activation, compared to dyes known to date.

Cleavage of amphiphile precursors by a certain enzyme can be determined by known methods, e.g. using thin layer chromatography.

The invention, finally, also relates to the above-described voltage-sensitive dye precursors of the formula (1), especially those which have at least one hydrophilic residue at the amine terminus (which actually represents the hydrophobic side of the molecule). Further, dye precursors are preferred in which $R^1$ and $R^2$ are a $C_{10}$-$C_{20}$, in particular, a $C_{10}$-$C_{14}$ hydrocarbon group. Further, dye precursors are especially preferred which contain at least one group Y at the tail.

The invention, in particular, relates to cell-selective staining that relies on extracellular application of an organic precursor dye and its local activation at a selected cell by a genetically encoded enzyme. Such an activation could rely on an induction of fluorescence quantum yield, of voltage sensitivity or on an induction of the interaction with the membrane. The latter approach is particularly attractive because the crucial chemical structure of the voltage-sensitive chromophore is not affected by enzymatic activation. As shown in FIG. 1, a nerve cell in brain tissue is genetically induced to express a membrane-bound enzyme with its active site facing the extracellular space. That ectoenzyme cleaves off a polar group of a water soluble precursor dye such that the overall lipophilicity of the dye is enhanced. As a consequence, the voltage-sensitive dye binds to the adjacent cell membrane.

The present invention is further demonstrated by induced membrane binding of a voltage-sensitive dye using a water soluble enzyme. In the test system we studied a modified styryl hemicyanine Di-4-ASPBS[6] (dye 1), with its sulfonium headgroup replaced by a phosphate group (dye 2, Di-4-ASPP phosphate). Hydrolysis of Di-4-ASPP phosphate leads to Di-4-ASPP alcohol (dye 3). The phosphate was chosen for two reasons: (i) It has a high polarity due to its two negative charges in moderately alkaline solution, with acidity constants of phosphate monoesters being $pK_{a1} \approx 1$ and $pK_{a2} \approx 6$[18]. (ii) Activation relies on alkaline phosphatase, an enzyme with a broad range of substrate specifity[19]. At first we characterized the partition coefficient of the dyes between water and membrane in suspensions of liposomes. Then, the cleavage of the phosphate appendix by alkaline phosphatase from the human placenta (PLAP) was studied by liquid chromatography and isothermal titration calorimetry. Combining these two elements, enzyme induced binding was implemented with liposomes. Finally the staining method was tested with individual giant lipid vesicles and red blood cells.

Figure 11:
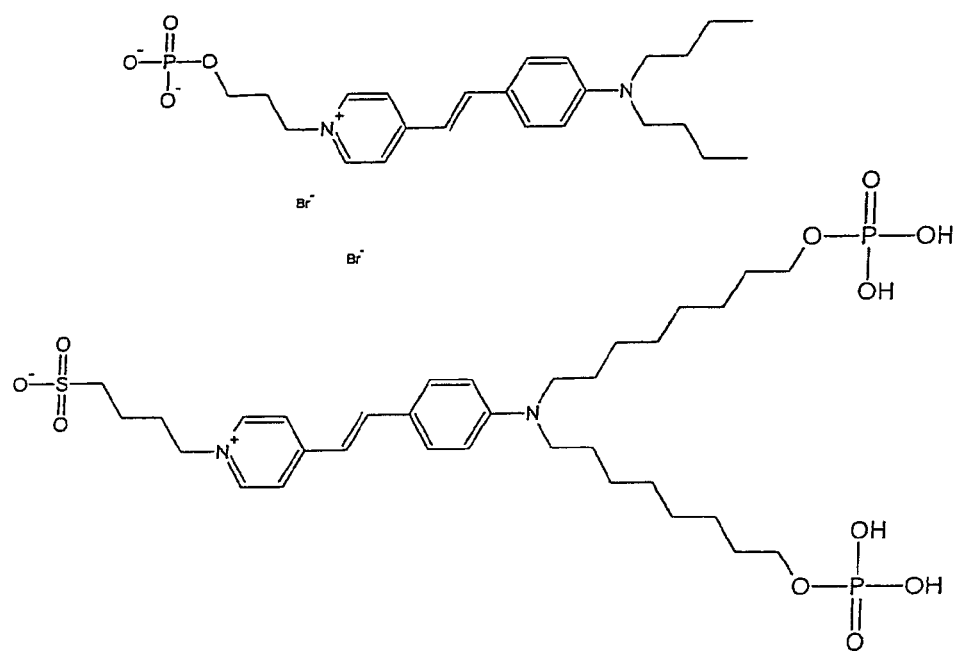

By making dye precursors with phosphate groups at the lipophilic tail, a much more pronounced difference in membrane binding strength between dye precursor and acticated dye was achieved (Di-8P-ASPBS, FIG. 11; Di-10P-ASPBS and Di-10A-ASPBS, FIG. 12; Di-12P-ASPBS and Di-12A-ASPBS, FIG. 13).

Surprisingly, the dyes which were modified at the lipophilic tail by addition of a hydroxyl linker and an increased length of the hydrocarbon chain were cell impermeable, in contrast to the dyes Di-4-ASPBS, Di4-ASPPP and Di-4-ASPPA. Unexpectedly, the crucial orientation of the dyes in the membrane was not affected by the additional hydroxyl residues as determined by polarised fluorescence experiments on giant vesicles and mammalian cells.

With Di-8P-ASPBS, enzyme induced staining of cells with soluble enzyme was demonstrated (FIG. 12).

Enzyme induced staining of cells by overexpressed enzyme was demonstrated on HEK293 cells and MDCK cells overexpressing a fusion protein of ArtPlasMA and PLAP. For these experiments, the dyes Di-8P-ASPBS (FIG. 13), Di-10P-ASPBS (FIG. 16, FIG. 19) and Di-12P-ASPBS (FIG. 17 to 19) were employed. Clearly, the selectivity of the reaction increased with increasing length of the hydrocarbon tail, i.e. the best selectivity was achieved with Di-12P-ASPBS as a precursor dye.

The invention is further explained in the Figures and Examples.

FIG. 1. Concept for enzyme induced selective staining of cells. (A) The two components are a voltage-sensitive dye derivatized with an enzymatically cleavable appendix, e.g. to the polar head group (represented by a circle) and an ectoenzyme expressed on the surface of a selected cell in a tissue symbolized by three cells. (B) The dye is hydrolysed by the ectoenzyme. Upon cleavage of the appendix, the dye binds to the membrane. (C) Cleaved dye accumulates in the membrane of that cell where it was produced.

Figure 2:
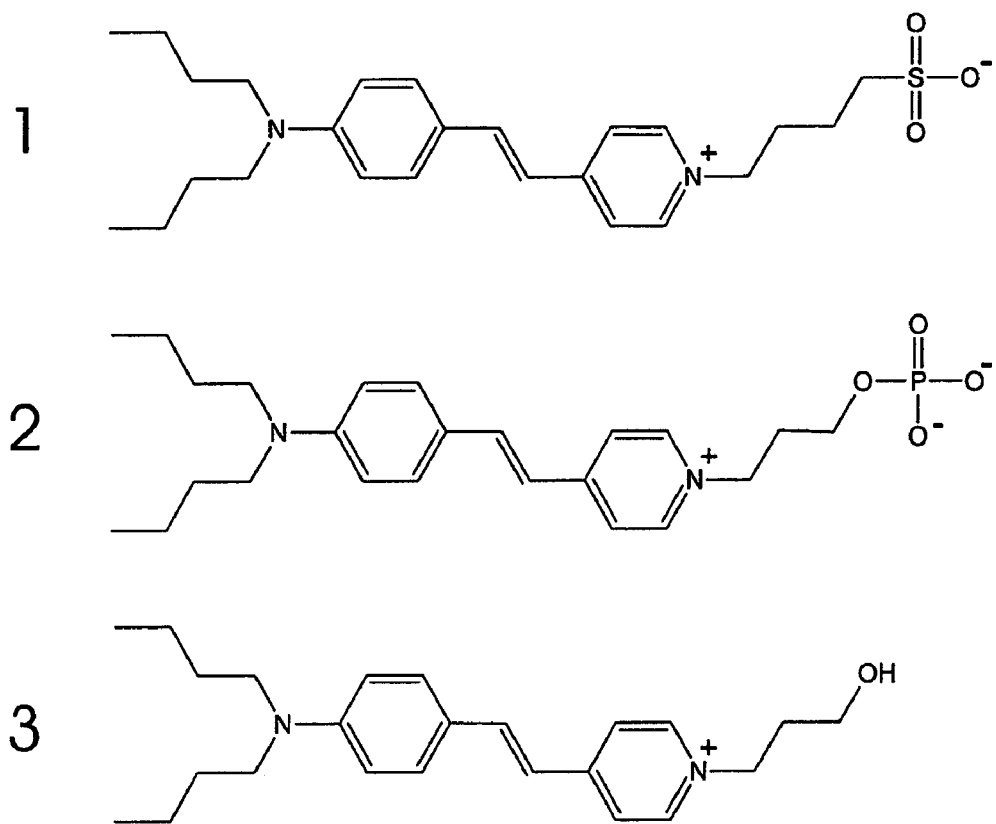

FIG. 2. Precursor dye with a cleavable group at the polar head group appendix. Voltage-sensitive hemicyanine dyes of the Dibutyl-aminostyryl-pyridinium (Di-4-ASP) type: (1) the common Di-4-ASP butylsulfonate (Di-4-ASPBS), (2) the substrate of enzyme activation Di-4-ASP propylphosphate (Di-4-ASPPP) and (3) the product of enzyme activation Di-4-ASP propylalcohol (Di-4-ASPPA).

Figure 3:
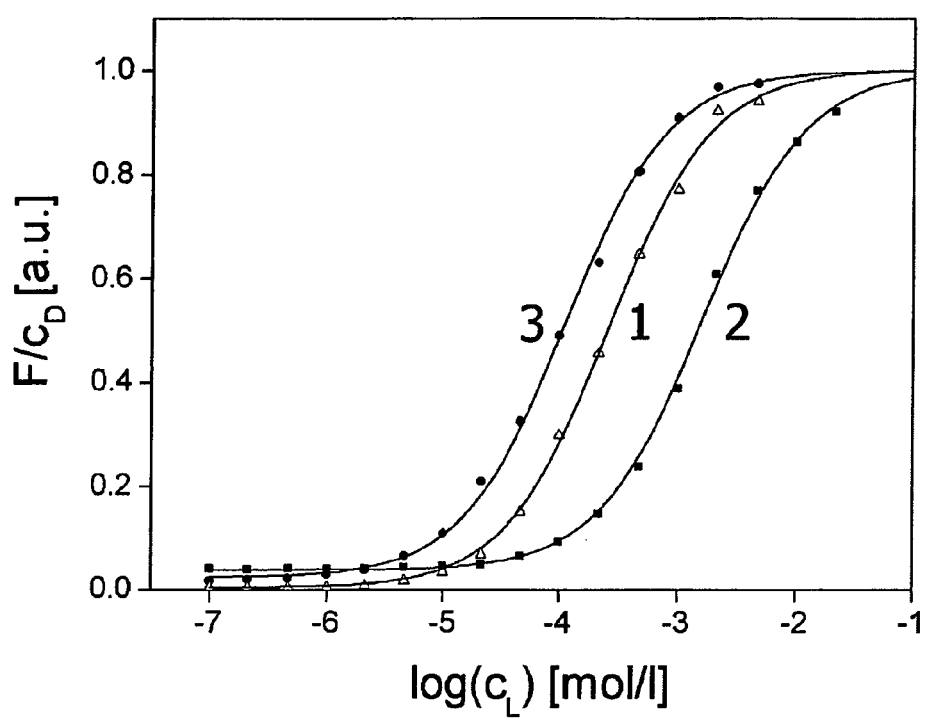

FIG. 3. Fluorescence titration with lipid. Ratio $F/c_D$ of fluorescence intensity and total concentration of dye versus logarithm of lipid (POPC) concentration $C_L$ in a dispersion of lipid vesicles. The figure shows typical measurements for Di-4-ASPBS (1), Di-4-ASPP phosphate (2) and Di-4-ASPP alcohol (3). The data are fitted by a partitioning equilibrium with a molecular binding constant $K_D$ and specific fluorescence intensities $f_{D,f}$ and $f_{D,b}$ of free dye in water and bound dye in lipid. For sake of clarity, the data were normalized to $f_{D,b}=1$ for each dye.

Figure 4:
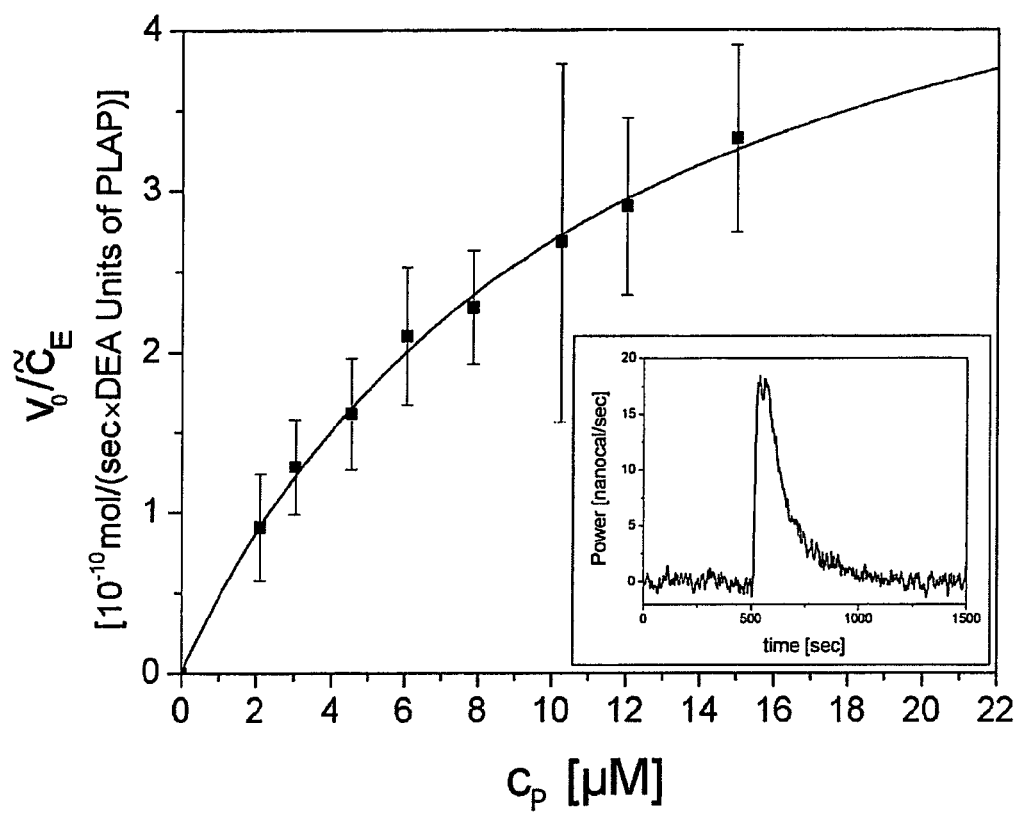

FIG. 4. Enzyme kinetics by microcalorimetry. Ratio $v_0/\tilde{c}_E$ of initial velocity of hydrolysis and of effective enzyme concentration versus concentration $C_P$ of the substrate Di-4-ASPP phosphate at 25.0° C. The data are fitted with Michaelis-Menten parameters $K_m$ and $\tilde{k}_{cat}$. Insert: Example for a microcalorimeter tracing of reaction heat versus time after subtraction of baseline and heat of dilution ($c_p$=6.1 μM). The peak of the curve corresponds to the initial velocity. The molar heat of reaction is obtained by integration.

Figure 5:
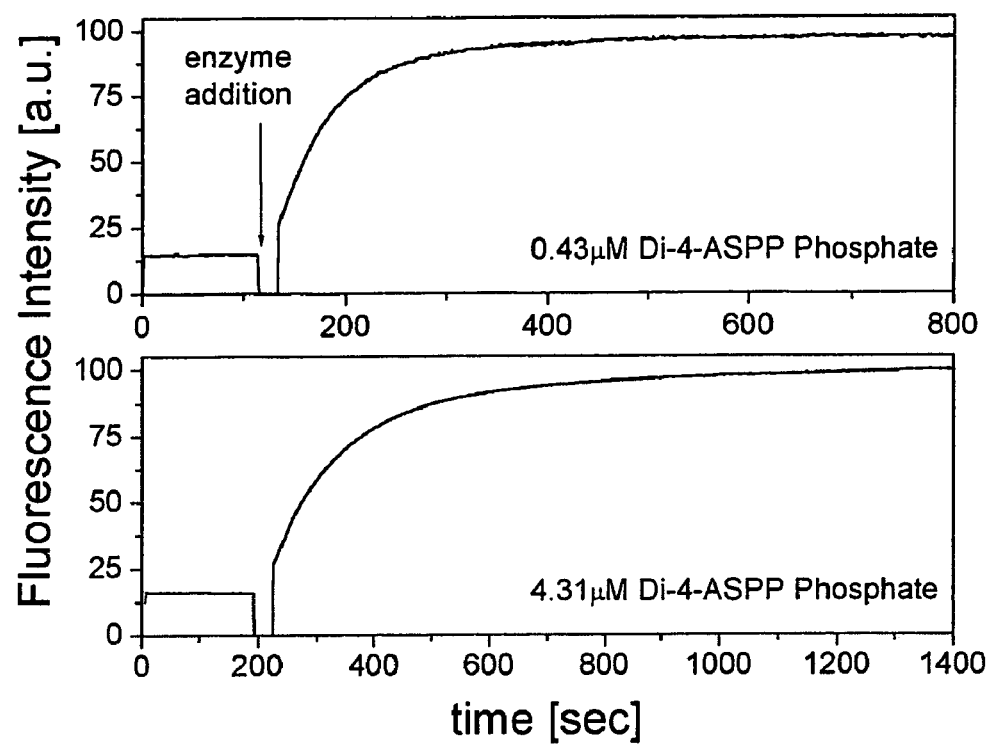

FIG. 5. Enzyme induced staining of lipid membrane. Fluorescence intensity versus time of a vesicle suspension (lipid concentration 100 μM POPC) at two concentrations 0.43 μM (top) or 4.31 μM (bottom) for the substrate Di-4-ASPP phosphate. The addition of phosphatase is marked by an arrow.

Figure 6:
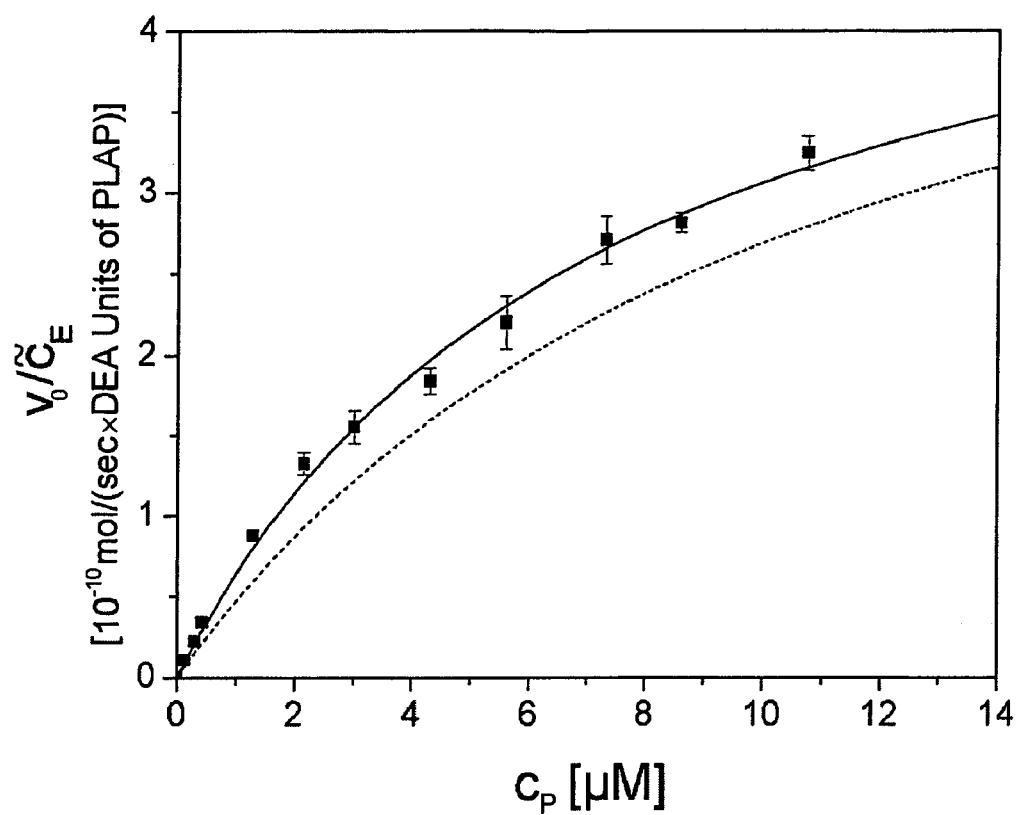

FIG. 6. Enzyme kinetics by fluorometry in a vesicle suspension. Ratio $v_0/\tilde{c}_E$ of initial velocity of hydrolysis and of effective enzyme concentration versus concentration $c_P$ of the substrate Di-4-ASPP phosphate at a lipid concentration of 100 μM (25.0° C.). The data are fitted with Michaelis-Menten parameters $K_m$ and $\tilde{k}_{cat}$. The fit obtained from microcalorimetric experiments (FIG. 4) is indicated as a dashed line.

Figure 7:
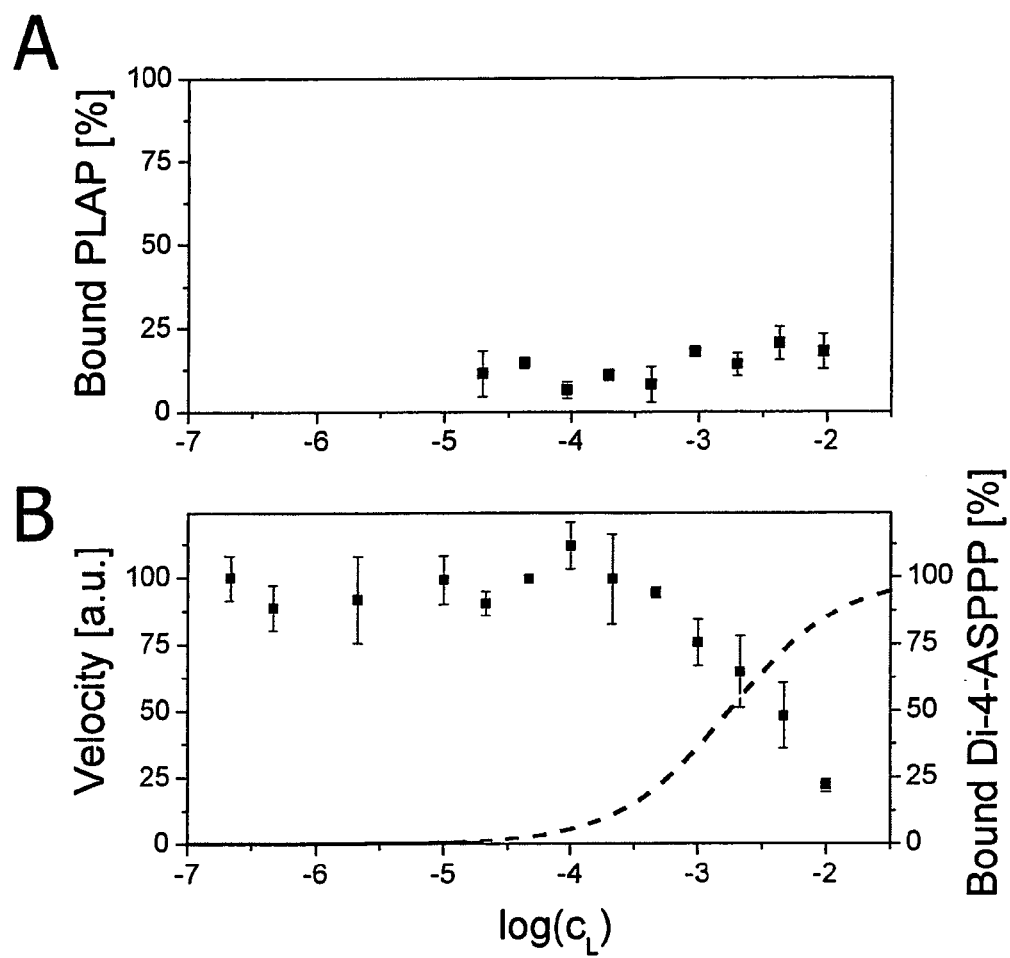

FIG. 7. Perturbation of enzyme kinetics by lipid bound enzyme and lipid bound substrate. (A) Percentage of bound enzyme PLAP versus lipid concentration determined by a sucrose loaded vesicle binding assay. The fraction of bound phosphatase is not significant considering the accuracy of the method (see text). (B) Reaction rate of enzymatic hydrolysis Di-4-ASPP phosphate versus lipid concentration. For comparison, the fraction of lipid bound substrate according to a partitioning equilibrium is plotted as a dashed line.

Figure 8:
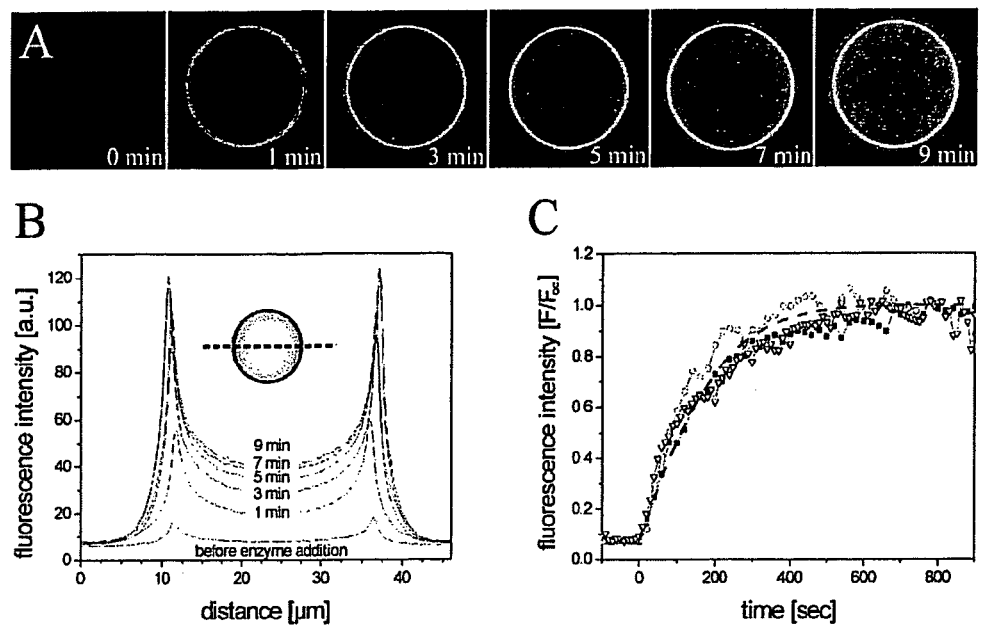

FIG. 8. Enzyme induced staining of giant lipid vesicle. (A) Fluorescence image (excitation around 450 nm, emission at >510 nm) of a giant vesicle before (0 min) and after addition of phosphatase (activity 0.18 DEA Units/ml). Di-4-ASPP phosphate was present at a concentration of 9.8 μM. (B) Profiles of fluorescence intensity across the diameter (approx.

27 μm) of a vesicle. (C) Normalized fluorescence intensity of vesicle membrane (peak of the profile minus background) versus time for three different vesicles. The dashed line is the fluorescence computed with the enzyme kinetic parameters $K_m$ and $k_{cat}$ from lipid vesicles and from ITC and a scaling factor of fluorescence fitted to the data.

Figure 9:
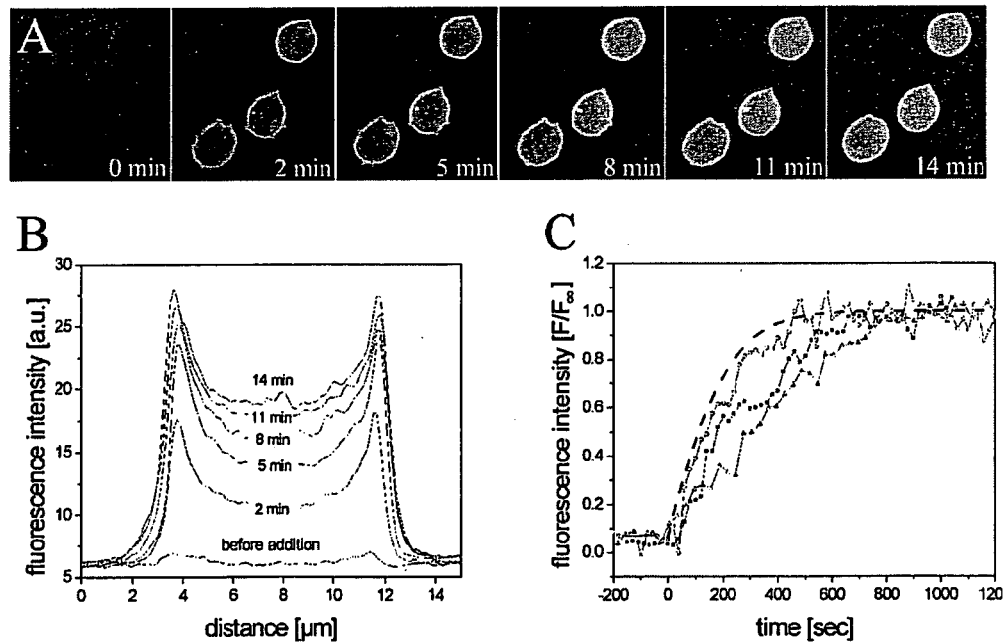

FIG. 9. Enzyme induced staining of erythrocyte membrane. (A) Fluorescence image (excitation around 450 nm, emission at >510 nm) of an erythrocyte before (0 min) and after addition of phosphatase (activity 0.18 DEA Units/ml). Di-4-ASPP phosphate was present at a concentration of 9.8 μM. (B) Profiles of fluorescence intensity across the diameter of an erythrocyte with a diameter of about 8 μm on the culture dish. (C) Normalized fluorescence intensity of vesicle membrane (peak of the profile minus background) versus time for three different vesicles. The dashed line is the fluorescence computed with the enzyme kinetic parameters $K_m$ and $k_{cat}$ from ITC and a scaling factor of fluorescence fitted to the data.

Figure 10:
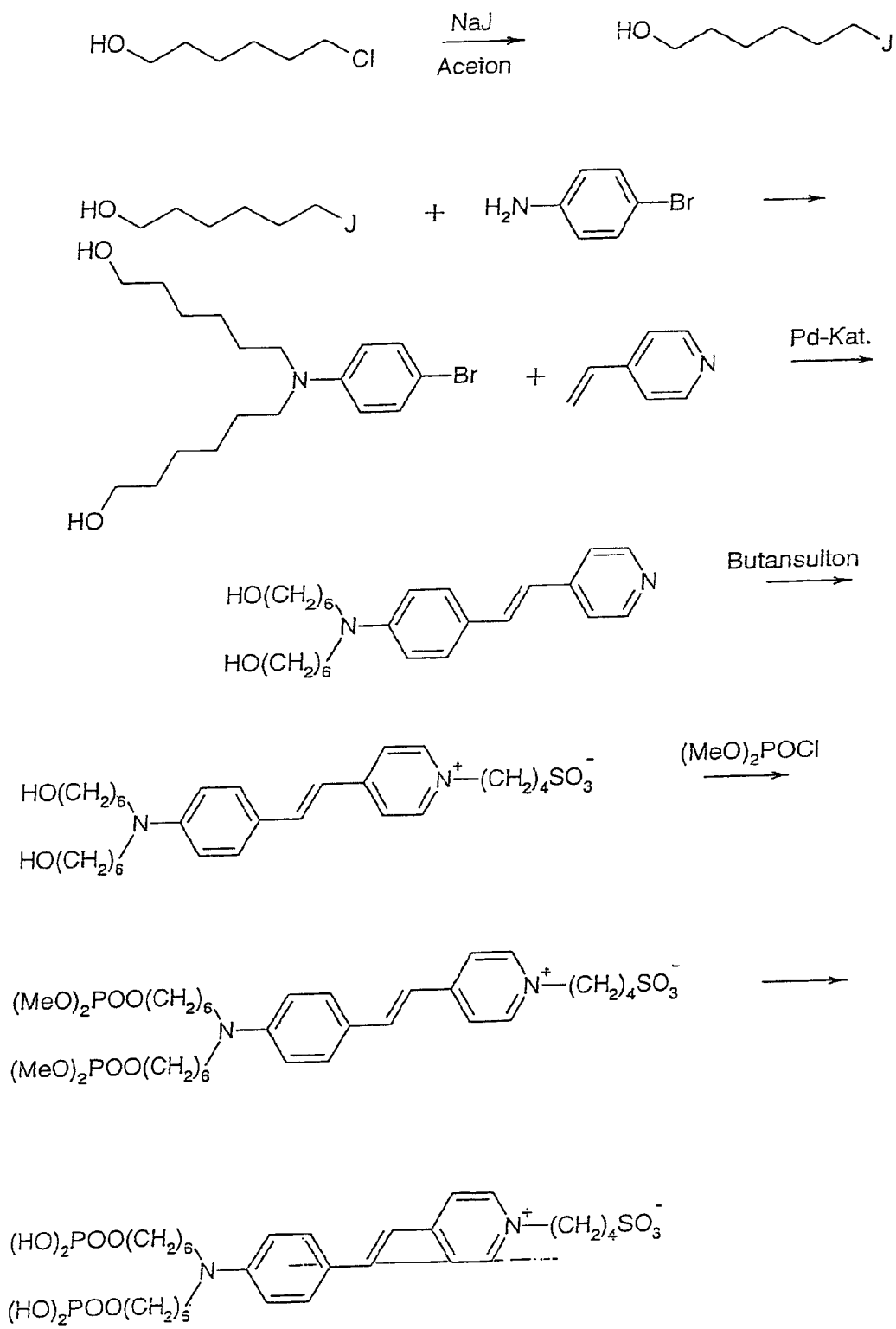

FIG. 10: Synthesis of dyes containing one or more groups Y within the residues $R^1$ and/or $R^2$ FIG. 11: Examples of enzymatically cleavable dye precursors.

FIG. 12A to F: Staining of HEK 293 cells with a voltage sensitive dye by activation of binding through soluble phosphatase added to the incubation medium. HEK 293 cells (A, brightfield image) were incubated with the voltage sensitive fluorescent dye Di-8-phosphato-ASPBS (cf. FIG. 11, bottom) at a concentration of 19.6 μM. B: After 30 minutes, no membrane fluorescence could be detected. The cell interior was stained only slightly, demonstrating that the dye permeates the cell plasma membrane very slowly. C to F: After addition of soluble PLAP (activity 0.18 DEA Units/ml) to the incubation medium, membrane fluorescence was activated and increased over time (C to F: 15 sec, 2 min, 4 min and 6 min after enzyme addition, respectively; excitation filter 450/50 nm, emission filter 510 nm longpass; dichroic mirror: 505 nm). The images shown are optimized for contrast and intensity.

FIG. 13A to C: Staining of transfected HEK 293 cells with a voltage sensitive dye by activation of binding through an overexpressed, membrane-bound phosphatase. HEK 293 cells were cotransfected with a vector coding for GFP and a vector coding for a fusion protein of a plasma membrane anchor and phosphatase from the human placenta. A. fluorescence image showing the GFP fluoresence of a transfected cell (excitation filter 450/50 nm, emission filter 510 nm longpass; dichroic mirror: 505 nm). B. The voltage sensitive fluorescent dye Di-8-phosphato-ASPBS (cf. FIG. 11, bottom) was added to the incubation medium. Directly after addition, no membrane fluorescence was visible (exc. 535/50 nm, em. 610/75 nm; dichroic mirror: 535 nm). C. After 5 min of incubation, the membrane of the transfected cell was clearly stained. Untransfected control cells incubated with the dye did not show any membrane fluorescence. The images shown are optimized for contrast and intensity.

Figure 14:
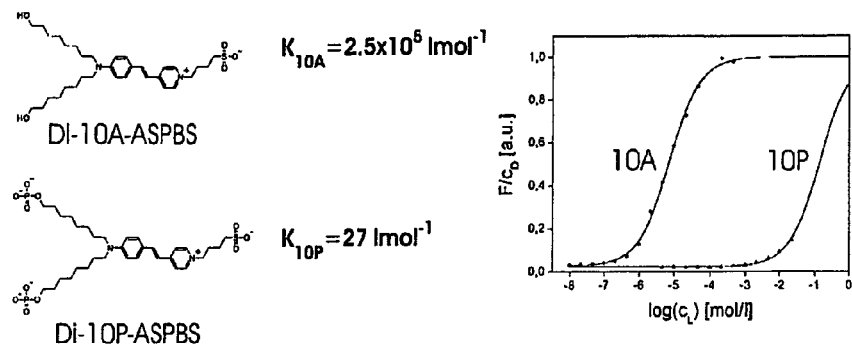

FIG. 14. Structure and lipid binding of the dyes Di-10A-ASPBS and Di-10P-ASPBS. Left: Structure of the dyes. Center: Fitted binding constants. Right: Fluorescence Titration with lipid.

Figure 15:
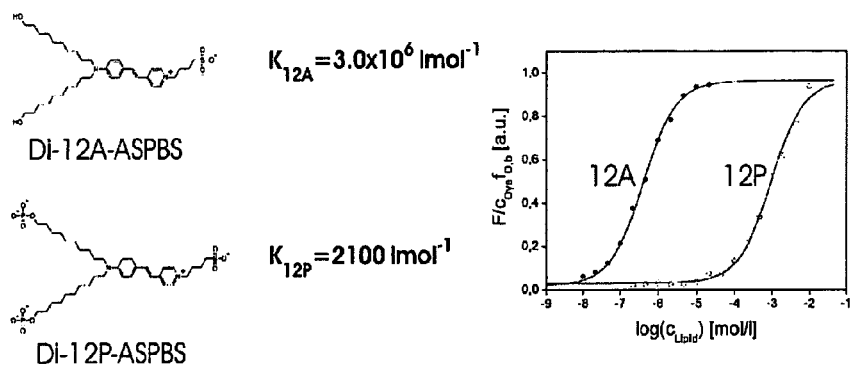

FIG. 15. Structure and lipid binding of the dyes Di-12A-ASPBS and Di-12P-ASPBS. Left: Structure of the dyes. Center: Fitted binding constants. Right: Fluorescence Titration with lipid.

Figure 16:
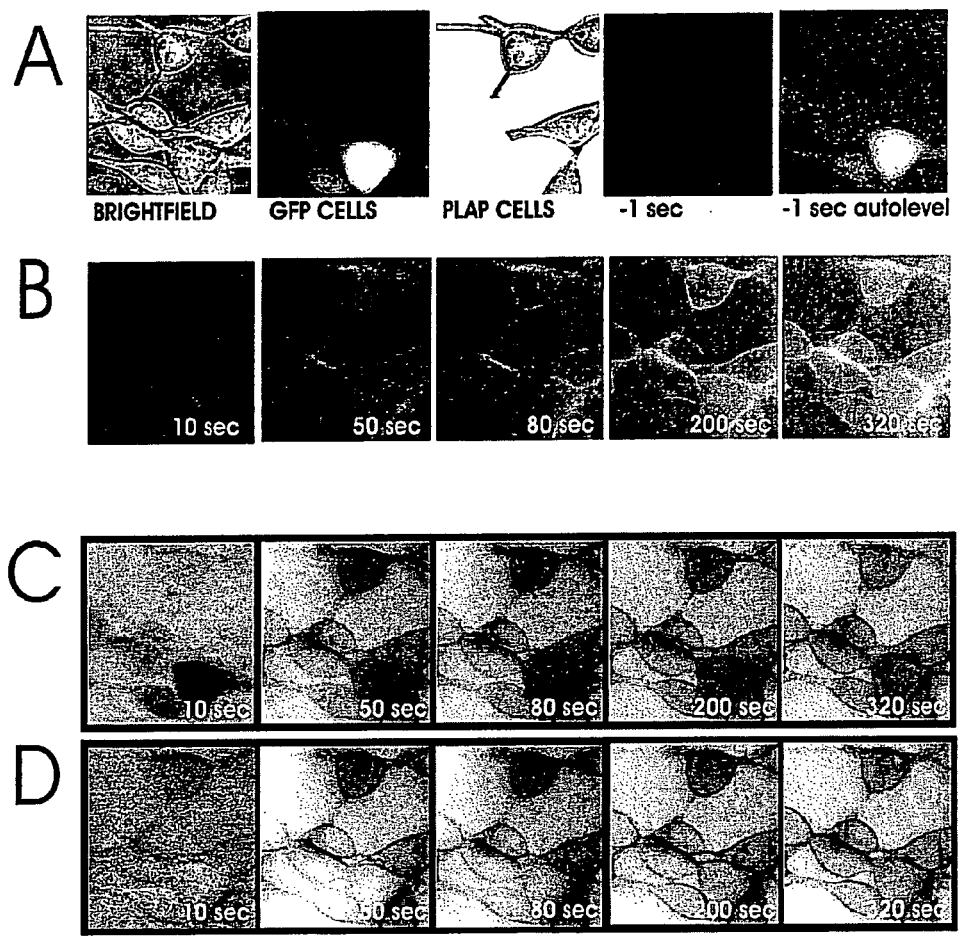

FIG. 16. Genetically Targeted Staining of HEK293 cells with 1 mM Di-10P-ASPBS. A mixture of stable clones either expressing the membrane-bound phosphatase construct or cytosolic GFP were cultured on the same dish. (A) From left to right: (i) Brightfield image of cells. (ii) Fluorescence image of cells showing cells expressing cytosolic GFP (excitation filter 450/50 nm, emission filter 510 nm, dichroic mirror 505 nm). (iii) Cells expressing phosphatase as obtained by subtraction of GFP expressing cells from image i. (iv) Fluorescence image of cells with filters exc. 535/50 nm, em. 610/75 nm; dichroic mirror 535 nm. The image is normalized to the same level as in row B. (v) autoleveled image iv, showing fluorescence crosstalk of GFP. (B) Enzyme induced staining of cells as measured with filter set exc. 535/50 nm, em. 610/75 nm; dichroic mirror 535 nm. The membrane fluorescence increases over time. (C). Inverted and contrast-enhanced fluorescence images corresponding to row B. (D) Difference images. The image A/iv was subtracted from the images in row B. The resulting images were inverted and contrast was enhanced.

Figure 17:
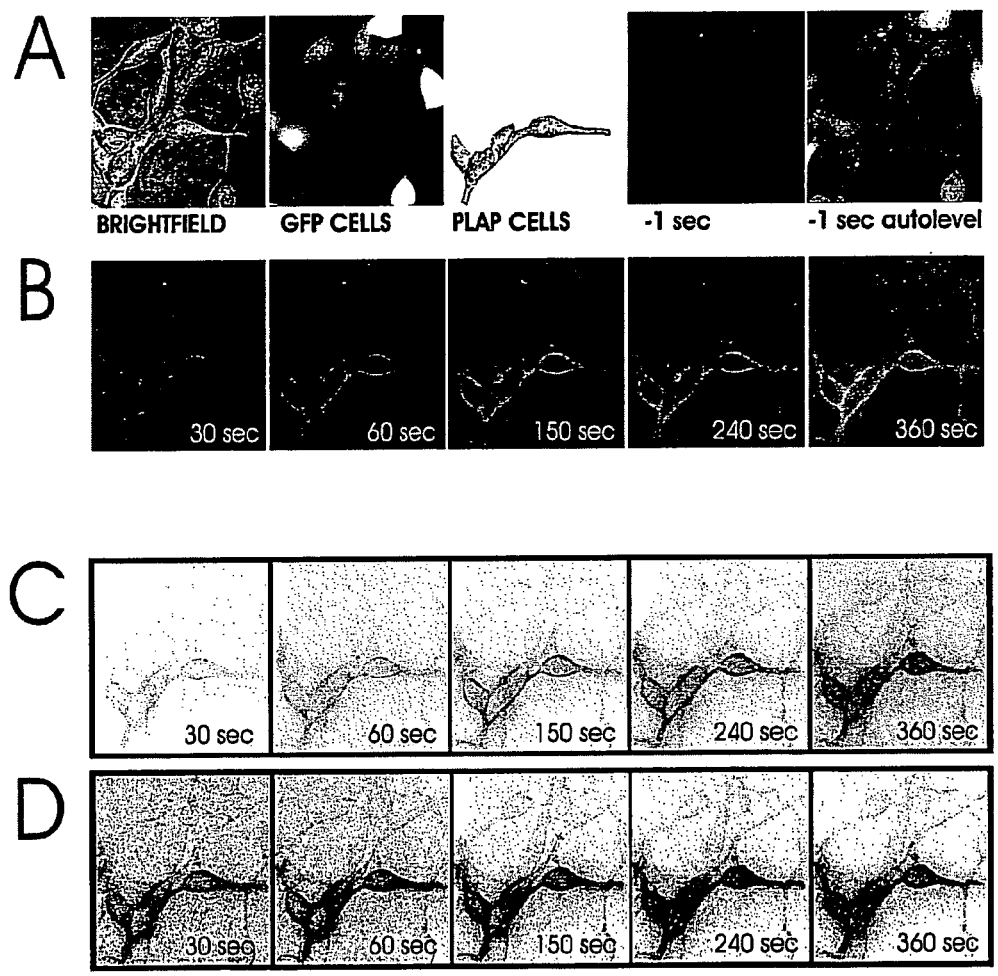

FIG. 17. Genetically Targeted Staining of HEK293 cells with 200 nM Di-12P-ASPBS. A mixture of stable clones either expressing the membrane-bound phosphatase construct or cytosolic GFP were cultured on the same dish. (A) From left to right: (i) Brightfield image of cells. (ii) Fluorescence image of cells showing cells expressing cytosolic GFP (excitation filter 450/50 nm, emission filter 510 nm, dichroic mirror 505 nm). (iii) Cells expressing phosphatase as obtained by subtraction of GFP expressing cells from image i. (iv) Fluorescence image of cells with filters exc. 535/50 nm, em. 610/75 nm; dichroic mirror 535 nm. The image is normalized to the same level as in row B. (v) autoleveled image iv, showing fluorescence crosstalk of GFP. (B) Enzyme induced staining of cells as measured with filter set exc. 535/50 nm, em. 610/75 nm; dichroic mirror 535 nm. The membrane fluorescence increases over time. (C). Inverted difference images. The image A/iv was subtracted from the images in row B. The resulting images were inverted and contrast was enhanced. (D) Contrast enhanced images of row C.

Figure 18:
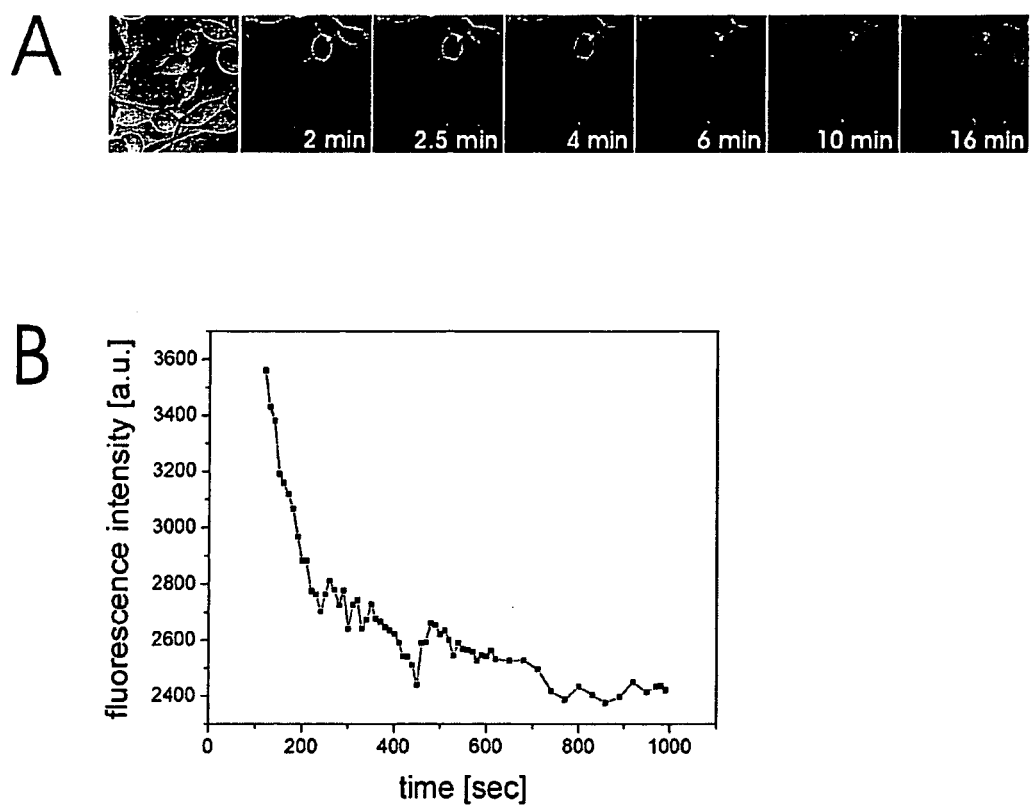

FIG. 18. Destaining. Cells were incubated with Di-12P-ASPBS for 30 seconds, then the medium containing the dye precursor was removed and the cells were washed twice in buffer containing no dye. Fluorescence images were recorded with excitation filter 450/50 nm, emission filter 510 nm, dichroic mirror 505 nm. A. Brightfield image of cells and fluorescence images of cells illustrating destaining of the cell membrane by diffusion of the dye into the bulk medium. B. Time course of destaining. The maximum fluorescence intensity of the membrane is plotted vs. time.

Figure 19:
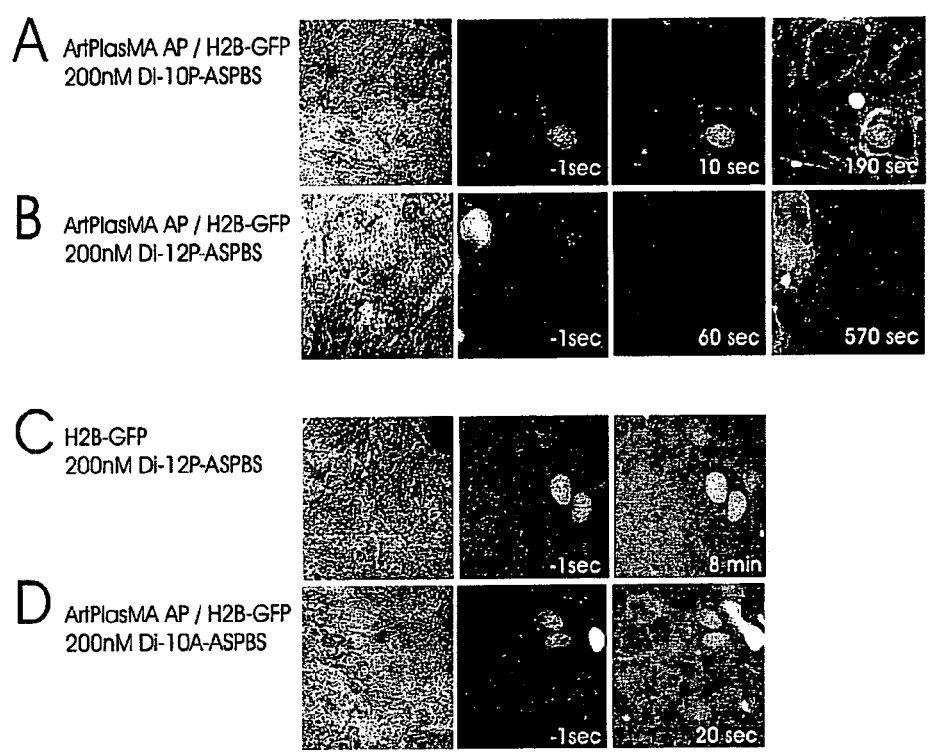

FIG. 19. Genetically Targeted Staining of MDCK cells with Di-10P-ASPBS and Di-12P-ASPBS. (A) Cells were cotransfected with the membrane-bound phosphatase construct termed ArtPlasMA AP and H2B-GFP, a nucleus-localized transfection marker. Brightfield image and fluorescence images before (−1 sec) and after addition of 200 nM Di-10P-ASPBS. (B) Analogous to row A, but using 200 nM Di-12P-ASPBS. (C) Control experiment. Cells were transfected only with H2B-GFP and incubated with 200 nM Di-12P-ASPBS. Brightfield image and fluorescence images before (−1 sec) and after addition of dye (8 min). (D) Control experiment. Cells were cotransfected with the membrane-bound phosphatase construct termed ArtPlasMA AP and H2B-GFP and incubated with the dye Di-10A-ASPBS. Brightfield image and fluorescence image before (−1 sec) and after addition of dye (20 sec).

EXAMPLES

Example 1

Dye. Di-4-ASPBS was synthesized as described in the literature[20]. Di4-ASPP alcohol (1-[γ-hydroxypropyl]-trans-4-[p-(di-n-butylamino)styryl]-pyridinium bromide) was obtained by reaction of trans-4-[p-(di-n-butylamino) styryl] pyridine (Di4-ASP) with 1.5 mole equivalents of 1-bromopropanol (100° C., 2 h). Subsequent precipitation of the product from methanol with diethylether and digeration in ethylacetate yielded Di-ASPP alcohol as a red solid. It was purified by column chromatography ($SiO_2$, $CHCl_3$:MeOH:$H_2O$ 50:20:4) and identified by NMR and mass spectrometry: $^1$H-NMR (400 MHz, $CDCl_3$) δ ppm 8.97 (d, 2H, $^3J=5.2$ Hz), 7.785 (d, 2H, $^3J=5.2$ Hz), 7.58 (d, 1H, $^3J=15.6$ Hz), 7.48 (d, 2H, $^3J=7.8$ Hz), 6.81 (d, 1H, $^3J=15.6$ Hz), 6.62 (d, 2H, $^3J=7.8$ Hz), 4.80 (s, br, 2H), 4.44 (s, br, 1H), 3.71 (t, 2H, $^3J=5.0$ Hz), 3.32 (s, br, 4H), 2.27 (t, 2H, $^3J=5.0$ Hz), 1.58 (s, br, 4H), 1.36 (q, 4H, $^3J=7.0$ Hz), 0.96 (t, 6H $^3J=7.0$ Hz); EIMS m/z 367.2 $M^+$ ($C_{24}H_{35}N_2O^+$ requires 367.6).

The first step of the synthesis of Di-ASPP phosphate (1-[γ-phosphatopropyl]-trans-4-p-[di-n-butylamino)-styryl]-pyridinium betaine) leads to Di-4-ASPP dimethylphosphate by reaction of Di-4-ASPP alcohol with 1.6 mole equivalents dimethylchlorophosphate in pyridine (16 h, room temperature). After evaporation of the solvent, the red intermediate product was purified by chromatography on a silica column ($CHCl_3$:MeOH:$H_2O$ 60:20:1). The phosphate was deprotected with 5 mole eq. dimethylsulfide and 17 mole eq. methanesulfonic acid by stirring overnight at room temperature. Upon neutralization with 25% $NH_3$, the colorless solution turned red. After evaporation, the red product was purified by column chromatography ($SiO_2$, $CHCl_3$:MeOH:$H_2O$ 50:20:4; Sephadex LH 20, MeOH). It was identified by NMR and mass spectrometry: $^1$H-NMR (400 MHz, MeCN) δ ppm 8.60 (s, br, 2H,), 7.72 (s, br, 2H,), 7.50 (d, 1H, $^3J=15.5$ Hz), 7.355 (d, 2H, $^3J=7.8$ Hz), 6.71 (d, 1H, $^3J=15.5$ Hz), 6.51 (d, 2H,$^3J=7.8$ Hz), 4.525 (s, br, 2H), 3.925 (s, br, 2H), 3.20 (s, br, 6H, O—H, N—$CH_2$), 2.17 (s, br, 2H), 1.445 (s, br, 4H), 1.26 (m, 4H), 0.87 (t, 6H, $^3J=7.2$ Hz); $^{31}$P-NMR (162 MHz, $CDCl_3$) δ ppm 4.59; EIMS m/z 447.2 $M^+$ ($C_{24}H_{36}N_2O_4P^+$ requires 447.5).

The absorption maximum of Di-4-ASPP alcohol in Tris-NaCl buffer (20 mM Tris, 100 mM NaCl, pH 8.1) was at 482 nm with an extinction coefficient of $3.91 \times 10^4$ $M^{-1}$ $cm^{-1}$ (Varian Cary 3E spectrometer, Mulgrave, Victoria, Australia). For Di-4-ASPP phosphate (FW=447.5) in the same buffer we found an extinction coefficient of $3.40 \times 10^4$ $M^{-1}$ $cm^{-1}$ at 479 nm. According to NMR data the preparation contained no organic impurities. An elementary analysis performed was in good agreement with the assumption that Di-4-ASPP phosphate contained 4 water molecules per dye, where we found C: 55.8% (55.6% expected for Di-4-ASPP phosphate×4 $H_2O$), H:8.2 (8.4), N: 5.5 (5.6); P:5.7 (6.0)}. For Di-4-ASPP phosphate×4 $H_2O$ (FW=519.5), the extinction coefficient corresponds to $3.95 \times 10^4$ $M^{-1}$ $cm^{-1}$. Solutions of defined concentration were prepared assuming the extinction coefficients of the dyes to be equal.

Fluorescence measurements were performed with an SLM Aminco 8100 fluorescence spectrometer (Acton Research, Acton, Mass., USA) using an avalanche photodiode in the detection channel (Polytec, Waldbronn, Germany). The band widths for excitation and emission were 16 nm and 36 nm, respectively. All measurements were performed under magic angle conditions. This was done to exclude possible effects of lifetime dependent spectra on the detected signal due to common polarisation in the excitation and emission monochromator. The cuvette holder was kept at a temperature of 25° C. (LAUDA RM 6 Thermostat). The maxima of fluorescence excitation and emission in Tris-NaCl buffer were around 490 nm and 630 nm for both dyes. For dye bound to POPC membranes (Tris-NaCl, 10 mM POPC vesicles), the excitation maxima were shifted to around 475 nm (Di-4-ASPP alcohol) and 465 nm (Di-4-ASPP phosphate) and the emission of both dyes was shifted to 600 nm.

Dye-lipid binding. The binding of the dyes to lipid membranes was determined by fluorescence lipid titration[21] with large unilamellar vesicles (LUVs) made of 1-palmitoyl-2-oleoyl-phosphatidylcholine (POPC). The purity of the lipids was checked by 2-dimensional TLC[22]. The vesicles were made by extrusion[23] in Tris-NaCl buffer (20 mM Tris, 100 mM NaCl, pH 8.1), using an extrusion apparatus and polycarbonate filters with 100 nm pore size (both Avestin Europe, Mannheim, Germany). Vesicle size was determined by quasielastic light scattering using an argon ion laser (Spectra-Physics, Darmstadt, Germany), a photomultiplier (Brookhaven Instruments, Vienna, Austria) and a correlator (ALV-5000, Langen, Germany). The lipid concentration was determined by a chromogenic enzyme assay (Biomerieux, Marcy l'Etoile, France). The standard deviation of three concentration measurements for every vesicle preparation was always below 4%. Vesicles were stored under argon at 4° C. in 15 ml Falcon Centrifuge Tubes (BD Labware Europe, Le Pont de Claix, France) and used within three days.

To measure dye binding constants, we prepared 1 mM solutions of the dyes 1-3 by ultrasonication in Ethanol (1) or Tris-NaCl buffer (2,3). These stock solutions were diluted in Tris-NaCl buffer to a concentration of 1 μM. In the same buffer, suspensions of POPC vesicles with concentrations ranging from 100 nM to 10 mM were prepared by dilution of stock solutions. Dye and lipid were pre-thermostatted to 25° C. Equal volumes of both were mixed directly before measurement. The fluorescence emission recorded at 600 nm with excitation at 488 nm was used for the evaluation of the partition coefficients.

Enzyme. We used Alkaline Phosphatase from the Human Placenta (PLAP).

Enzyme kinetics with ITC. We performed enzyme kinetic measurements with Di-4-ASPP phosphate as a substrate of PLAP by isothermal titration calorimetry (ITC). We used Tris-NaCl buffer (20 mM Tris, 100 mM NaCl, pH 8.1) without $Zn^{2+}$ and $Mg^{2+}$ although most alkaline phosphatases depend on these metals for maximum activity. However, divalent cations bind to lipid membranes and induce their aggregation and fusion[25]. The pH-value is a compromise between optimal enzymatic activity (at pH 9.8) and compatibility with vesicles and cells. The microcalorimeter (VP-ITC, Microcal, Northampton, Mass., USA) was thermostatted to 25.0° C., with reference power set to 10 μcal/sec and a stirring speed of 310 rpm. The sample cell contained a PLAP solution of 0.19 DEA Units/ml activity and the syringe was filled with a 1 mM solution of Di-4-ASPP phosphate. The reference cell contained buffer only. Different amounts of dye were injected into the sample cell in separate experiments to cover a concentration range from 2 μM to 15 μM. To determine the heats of dilution alone, injections were carried out with pure buffer. For both hydrolysis and dilution, the baseline signal was approximated by linear or polynomial functions and subtracted from the raw signal resulting in a curve with a flat baseline. The dilution signal was subtracted from the signal of the enzymatic reaction to yield the final calorimeter tracing of enzymatic hydrolysis. The molar heat of reaction was obtained by integration. The initial velocities were determined from the average heat of reaction of the first 10 to 30 seconds after the onset of the reaction, using the mean molar heat of reaction as a proportionality constant. Data analysis, including estimates of statistical errors of nonlinear curve fits, was performed with Origin (OriginLab Software, Northhampton, Mass., USA).

Sucrose Loaded Vesicle Binding Assay. This assay[26] was used to study the binding of PLAP to lipid vesicles. Sucrose loaded vesicles were made by extrusion in 20 mM Tris, 176 mM Sucrose, pH 8.1. The outside buffer was exchanged by 1:4 dilution into sucrose-free Tris-KCl buffer (20 mM Tris, 100 mM KCl, pH 8.1) and ultracentrifugation for 1 h at 100,000 g and 25° C. (Optima TLX with a TLA-100.3 rotor, 1.5 ml polyallomer microfuge tubes, Beckman Coulter, Fullerton, Calif., USA). The pelleted vesicles were resuspended in Tris-KCl buffer and used the same day. The lipid concentration was determined by the chromogenic enzyme assay. For the binding assay, sucrose loaded POPC vesicles were diluted to concentrations ranging from 20 µM to 10 mM. To 550 µl lipid suspensions we added 5 µl of a PLAP solution of 18.6 DEA Units/ml activity in Tris-KCl buffer. After 45 minutes incubation at room temperature the suspensions were centrifugated. To account for protein loss during centrifugation, tubes containing no lipid were added as a reference. The supernatant was removed as completely as possible. The enzymatic activity in the supernatant of solutions with and without lipid was determined by using p-NPP as a substrate. 0.2 ml of the supernatant were added to 1.8 ml 1 mM p-NPP in Tris-KCl buffer and absorption over time was recorded at 405 nm. The fraction of bound phosphatase was obtained from the ratio (activity of supernatant without lipid–activity of supernatant with lipid)/activity supernatant without lipid.

Enzyme induced staining of liposomes. We studied enzymatic hydrolysis of Di-4-ASPP phosphate in the presence of large unilamellar POPC vesicles (LUVs) to observe enzyme induced staining. Tris-NaCl Buffer was used for the preparation of all solutions. To 550 µl of a 200 µM solution of POPC vesicles in a cuvette, an equal volume of Di-4-ASPP phosphate was added to yield concentrations between 0.1 µM and 10.7 µM. 10 µl of PLAP (18.6 DEA Units/ml) were added and the suspension was mixed by pipetting. The cuvette was held at 25° C. Fluorescence (excitation 488 nm, emission 600 nm) was recorded before and after addition of the enzyme with a resolution of 1 sec. Initial velocities were determined from the slope of the first 10 to 20 seconds of the fluorescence traces.

Enzyme induced staining of giant vesicles. Giant POPC vesicles were prepared by electroswelling[27,28]. 5 µl of a 2 mM lipid solution in diethylether/methanol (9:1, v/v) were applied to a pair of planar electrodes of indium tin oxide coated with 70 nm of silica. After evaporation of the solvent under reduced pressure (0.1 mbar), 2 ml of 300 mM sucrose were added and giant vesicle formation was promoted by applying AC voltage to the electrodes. After formation was complete, vesicles were transferred to 35 mm polypropylene cell culture dishes (BD Biosciences Europe, Le Pont de Claix, France) and diluted in the same buffer. They were used the same day.

For enzyme kinetic measurements at room temperature, 400 µl of the giant vesicle stock solution were transferred to a culture dish containing 3,600 µl buffer (20 mM Tris, 100 mM NaCl, 120 mM Glucose, pH 8.1). The dish had been treated overnight with poly-L-lysine (25 µg/l) to permit the immobilisation of vesicles. The giant vesicles were allowed to adhere to the substrate for 15 minutes. Subsequently, 40 µl of a 1 mM Di-4-ASPP phosphate solution in the same buffer were added. The fluorescence of a selected giant vesicle with a diameter of 10 to 40 µm was observed using a microscope (Axioskop, Zeiss, Oberkochen, Germany) equipped with a 100 water immersion objective and a b/w CCD camera (Sony ICX 285 Chip, Theta System, Gröbenzell, Germany). The light of a high pressure mercury lamp (Zeiss) was passed through a band pass (450/50 nm) and a dichroic mirror (505 nm). The fluorescence was detected through the dichroic mirror and a long pass filter (510 nm). Grey filters were used to reduce light intensity. The microscope was focused on the maximum diameter of the vesicles before and during the experiment. After incubation with the dye for 5 minutes, 40 µl of PLAP were added from a stock solution with an activity of 18.6 DEA Units/ml. Homogenous distribution was achieved by mild pipetting. Images were recorded every 10 or 20 seconds before and after addition of the phosphatase. Image acquisition, camera and shutter control as well as image analysis were performed with software written in Labview (National Instruments Germany, Munich).

Enzyme induced staining of red blood cells. Human erythrocytes were prepared according to a slightly modified standard procedure[29]. 4 ml of blood of MJH were sucked into a tube coated with EDTA (Vacutainer 367,861, Becton Dickinson, Meylan, France) and centrifuged for 10 min at 1600 g. The pellet (~1 ml) was washed three times by resuspension and centrifugation for 10 min at 1600 g using 15 ml of a 300 mOsm Tris buffer (50 mM Tris, 110 mM NaCl, pH 7.4). Finally, the pellet was diluted with an equal volume of the same buffer additionally containing 1 mM $CaCl_2$. $Ca^{2+}$ was added since it was found to increase the number of erythrocytes retaining a round shape under the experimental conditions.

The staining experiments with erythrocytes were similar to those with giant vesicles. 2 µl of the erythrocyte stock solution were spread on the bottom of an untreated culture dish containing Tris buffer with $CaCl_2$ (20 mM Tris, 100 mM NaCl, 70 mM Glucose, 1 mM $CaCl_2$, pH 8.1). After 30 seconds, erythrocytes not adhered to the substrate were removed by washing twice. The dish was filled with 4 ml buffer. 40 µl of a 1 mM Di-4-ASPP-phosphate solution were added. After 5 minutes incubation, 40 µl of PLAP were added from a stock solution with an activity of 18.6 DEA Units/ml. Images were taken every 30 seconds before and after the addition of the enzyme. To minimize UV exposure, erythrocytes were focused under red light before and, if necessary, during the experiment.

Dye binding to lipid. When styryl hemicyanines bind to lipid bilayers, their quantum yield of fluorescence is enhanced. Di-4-ASPBS, for example, shows a 36 fold increase in fluorescence quantum yield upon transfer from water to lecithin membranes[30]. We take advantage of that effect to examine the binding of Di-4-ASPP phosphate and Di-4-ASPP alcohol to lipid membranes by fluorescence titration[21]. For comparison Di-4-ASPBS was also included in the investigation.

Dispersions of large lipid vesicles (Ø≈100 nm) were made from palmitoyl-oleoyl-phosphatidylcholine (POPC) with lipid concentrations ranging over five orders of magnitude. Dye was added to a concentration of 0.5 µM and fluorescence was measured. The fluorescence intensity was enhanced with increasing concentration of lipid for all three dyes. The enhancement was shifted to higher lipid concentrations in the order Di-4-ASPP alcohol, Di-4-ASPBS and Di-4-ASPP phosphate.

The average binding constants are $K_A=17920\pm360 M^{-1}$ for the alcohol (n=5), $K_S=7500\pm440 M^{-1}$ for the sulfonate (n=2)

and $K_P$=1140±140 M$^{-1}$ for the phosphate (n=7). The binding constant decreases when the dye bears a negatively charged headgroup.

There is an increment of the binding energy between sulfonate and alcohol of $\Delta(\Delta G_{SA})$=−RT ln($K_S/K_A$)=2.2 kJ/mol as well as for phosphate and alcohol $\Delta$ ($\Delta G_{PA}$)=−RT ln($K_P/K_A$)= 6.8 kJ/mol. We assign that effect to a changed resolvation of the polar headgroup when the dye binds to the membrane. The polar headgroup is brought into the water/membrane interface with its lower polarity as compared to bulk water.[33] We may expect that thereby its solvation energy is reduced and that this effect is more significant for a headgroup bearing a net charge.

Enzymatic dye hydrolysis. We tested whether Di-4-ASPP phosphate was accepted as a substrate by the soluble alkaline phosphatase from the human placenta (PLAP). After incubation with the dye, the enzyme was removed by ultrafiltration. HPLC analysis showed that Di-4-ASPP phosphate was quantitatively converted to Di-4-ASPP alcohol. The reaction kinetics were studied by isothermal titration calorimetry (ITC). We evaluated the heat production per unit time that is proportional to the reaction rate, with the molar heat of reaction being the constant of proportionality[38]. We found that the hydrolysis was endothermal by 1.1±0.2 kJ/mol, a value in a typical range for monophosphoric acid esters[39]. By calibration with that energy, the initial reaction velocity was evaluated. We conclude that Di-4-ASPP phosphate is accepted by PLAP as a regular substrate.

Enzyme Induced staining of liposomes. Now, we combined the two previous experiments. The dye phosphate was hydrolysed by phosphatase in the presence of lipid vesicles. The reaction was observed by the enhancement of fluorescence due to the enhanced binding of the dye alcohol to the lipid. The fluorescence intensity of a vesicle suspension (100 μM lipid) was recorded before and after the addition of the phosphatase with 0.43 μM and 4.31 μM Di-4-ASPP phosphate. It was enhanced about sixfold from a low level caused by the binding of the substrate to a high level caused by binding of the product. This corresponds to the ratio of the fluorescence lipid titration data of alcohol and phosphate at 100 μM lipid. We conclude that staining of lipid membranes is accomplished by enzymatically induced enhancement of lipophilicity.

Enzyme Induced staining of giant vesicles. As a first example for enzyme induced staining of a cell-like system, we chose giant lipid vesicles (Ø≈10-40 μm). Individual vesicles of POPC were incubated with 9.8 μM of the dye phosphate and observed in a microscope with a CCD camera. The fluorescence of the membrane increases considerably after addition of the enzyme. That impressively demonstrates that enzyme induced staining is possible with individual cell-like structures.

We evaluated the intensity of a row of pixels of the image at the maximum diameter in y-direction. After addition of the enzyme the fluorescence increased from a constant low value $F_0$ caused by staining with the phosphate to a high constant value $F_\infty$ due to staining by the alcohol. The ratio of intensities was $F_\infty/F_0$=9-13.

The fluorescence intensity in a microscope that is focussed on the membrane is dominated by membrane-bound dye, i.e. by the density of bound dye molecules with little contribution of the solution. For liposome suspensions, we measured $K_A/K_P$≈16 at low dye concentrations and $K_A/K_P$≈7 at a concentration of 9.8 μM. The ratio of the fluorescence intensities $F_\infty/F_0$=9-13 found with giant vesicles is in good agreement.

During the reaction, the fluorescence is $F(t)=F_0[c_P(t)/c_{tot}]+F_\infty[1-c_P(t)/c_{tot}]$. We compute the dynamics of the normalized fluorescence $F/F_\infty$ by inserting the Michaelis-Menten dynamics and integrating it with the parameters determined by ITC. The result is plotted in FIG. 8C (dashed line). The perfect agreement with the data shows that staining of giant vesicles is indeed due to enzymatic activation of the precursor dye.

Enzyme induced staining of erythrocyte membrane. The plasma membrane of cells consists of a variety of charged and uncharged lipids and of membrane proteins. It is well known that voltage sensitive dyes are able to bind to membrane proteins[40]. Therefore it must be checked whether an enzyme induced change of headgroup polarity leads to increased staining of a eucaryote membrane. We chose erythrocytes as a model. Red blood cells have a rather inactive plasma membrane and no internal organelles.

Di-4-ASPP phosphate was added to human erythrocytes attached to a culture dish to a concentration of 9.8 μM. Membrane fluorescence was measured in the same setup as with giant vesicles. Fluorescence was weaker than with giant vesicles, which we attribute to fluorescence quenching by hemoglobin and the smaller size of the erythrocytes. FIG. 9A shows an example of a sequence of images of the erythrocyte membrane before and after addition of phosphatase. The fluorescence intensity significantly increased. The experiment proves that the enzyme induced modulation of headgroup polarity is an effective mechanism of staining also with cell membranes.

Plots of the intensity of a row of pixels cutting through the image of an erythrocyte at its maximum diameter are shown in B. The normalized maximum brightness minus the background signal versus time is shown in C. The ratio of final and initial fluorescence was $F_\infty/F_0$=11-25 with an average of 15. These values are similar to the fluorescence enhancement on giant vesicles. Also the fluorescence dynamics during staining that is computed from the Michaelis-Menten kinetics agrees fairly well with the experiments as shown in FIG. 9C. However, the variation of the experiments and the deviation from the expected reaction progress is larger than for giant vesicles. We think that there is a larger experimental error due to the weaker fluorescence and due to changes of shape of the erythrocytes during the measurement.

Example 2

Binding. The dyes Di-10-phosphato-ASPBS (Di-10P-ASPBS) and Di-12-phosphato-ASPBS (Di-12P-ASPBS) as well as the corresponding products after enzymatic hydrolysis Di-10-hydroxy-ASPBS (Di-10A-ASPBS) and Di-12-hydroxy-ASPBS (Di-12A-ASPBS) were synthesized by organic chemical methods. Their binding to lipid membranes was tested by fluorescence lipid titration (cf. page 15, section dye binding to lipid). The binding constants amounted to 27 M$^{-1}$ (Di-10P-ASPBS), 250,000 M$^{-1}$ (Di-10A-ASPBS), 2100 M$^{-1}$ (Di-12P-ASPBS) and 3,000,000 M$^{-1}$ (Di-12P-ASPBS) (FIGS. 14 and 15 (center and right hand side)). The difference in binding constants between dye alcohol and dye phosphates (or dye precursors) therefore amounted to a factor of 10,000 for the pair Di-10P-ASPBS/Di-10A-ASPBS and to a factor of 1000 for the pair Di-12P-ASPBS/Di-12A-ASPBS. The binding curve for the more lipophilic pair Di-12P-ASPBS/Di-12A-ASPBS is shifted to higher lipid concentrations.

Enzyme induced staining. The dye precursors Di-10P-ASPBS and Di-12P-ASPBS were used to effect enzyme induced staining on cells. To test whether the staining is selective, a mixture of two cell populations was cultured in the same dish. One of these stably expressed the phosphatase construct, while the other was stably expressing GFP as a negative marker. It was found that both dyes allowed enzyme induced membrane staining. However, the staining intensity and its confinement to phosphatase expressing cells was distinctly better for the more lipophilic precursor Di-12P-ASPBS (FIGS. 16 and 17).

Destaining. It was found that staining membranes with the presented method is a reversible process. Cells were incubated with Di-12P-ASPBS for 30 seconds, then the medium containing the dye precursor was removed and the cells were washed twice in buffer containing no dye. A selective staining of phosphatase expressing cells could be observed. Over time, the fluorescence intensity of the stained membranes declined due to diffusion of the bound dye to the bulk medium (FIG. 18). This experiment in addition demonstrates that the dye binds almost exclusively to the extracellular leaflet of the stained cells.

Enzyme Induced Staining of MDCK cells transiently transfected with a

Phosphatase. This experiment demonstrates that the presented method is applicable also to other cell lines: Madine Darby Canine Kidney (MDCK) cells were transiently transfected with the described membrane-bound phosphatase and cotransfected with the construct H2B-GFP as a nucleus-localized transfection marker. In an experiment using Di-10P-ASPBS, staining is localized to the transfected cells at the beginning of the experiment (FIG. 19A). However, during a time course of several minutes the produced dye diffuses to the surrounding, nontransfected cells. With Di-12P-ASPBS, the situation is different: Staining is well localized even after 10 minutes incubation with the precursor dye. Directly adjacent cells are weakly stained at this point of time (FIG. 19B).

Two control experiments were performed: In the first control, cells were transfected only with the transfection marker H2B-GFP. The cells were only weakly stained upon addition of Di-12P-ASPBS. In addition, no difference in staining intensity between transfected and untransfected cells can be discerned (FIG. 19C). In the second control experiment, cells were cotransfected with the phosphatase construct and the transfection marker. After addition of the dye Di-10A-ASPBS, transfected and untransfected cells are equally and unselectively stained, showing that selective staining in the experiments of FIGS. 19A and B was not a result of binding of the dye to overexpressed protein.

REFERENCES (1) Tasaki, I.; Watanabe, A.; Sandlin, R.; Carnay, L. *Proc. Natl. Acad. Sci. U.S.A.* 1968, 61, 883.
(2) Cohen, L. B.; Salzberg, B. M.; Davila, H. V.; Ross, W. N.; Landowne, D.; Waggoner, A. S.; Wang, C. H. *J. Membr. Biol.* 1974, 19, 1.
(3) Cohen, L. B.; Salzberg, B. M. *Rev. Physiol. Biochem. Pharmacol.* 1978, 35.
(4) Loew, L. M.; Bonneville, G. W.; Surow, J. *Biochemistry* 1978, 17, 4065.
(5) Loew, L. M.; Simpson, L. L. *Biophys. J.* 1981, 34, 353.
(6) Fluhler, E.; Burnham, V. G.; Loew, L. M. *Biochemistry* 1985, 24, 5749.
(7) Grinvald, A.; Hildesheim, R.; Farber, I. C.; Anglister, L. *Biophys. J.* 1982, 39, 301.
(8) Grinvald, A.; Fine, A.; Farber, I. C.; Hildesheim, R. *Biophys. J.* 1983, 42, 195.
(9) Hübener, G.; Lambacher, A.; Fromherz, P. *J. Phys. Chem. B* 2003, 107, 7896.
(10) Kuhn, B.; Fromherz, P. *J. Phys. Chem. B* 2003, 107, 7903.
(11) Bullen, A.; Saggau, P. Optical Recording from Individual Neurons in Culture. In *Modern Techniques in Neuroscience Research;* 1st ed.; Johannson, H., Ed.; Springer: Berlin, 1999; pp 89.
(12) Sinha, S. R.; Saggau, P. Optical Recording from Populations of Neurons in Brain Slices. In *Modern Techniques in Neuroscience Research;* 1st ed.; Johannson, H., Ed.; Springer: Berlin, 1999; Vol. Berlin; pp 459.
(13) Grinvald, A.; Shoham, D.; Shmuel, A.; Glaser, D.; Vanzetta, I.; Shtoyerman, E.; Slovin, H.; Wijnbergen, C.; Hildesheim, R.; Arieli, A. In Vivo Optical Imaging of Cortical Architechture and Dynamics. In *Modern Techniques in Neuroscience Research;* Johannson, H., Ed.; Springer: Berlin, 1999; Vol. 1st; pp 893.
(14) Grinvald, A.; Salzberg, B. M.; Lev-Ram, V.; Hildesheim, R. *Biophys. J.* 1987, 51, 643.
(15) Antic, S.; Zecevic, D. *J. Neurosci.* 1995, 15, 1392.
(16) Siegel, M. S.; Isacoff, E. Y. *Neuron* 1997, 19, 735.
(17) Sakai, R.; Canonigo, V. R.; Raj, C. D.; Knöpfel, T. *Eur. J. Neurosci.* 2001, 13, 2314.
(18) Massoud, S. S.; Sigel, H. *Inorg. Chem.* 1988, 27, 1447.
(19) Georgatsos, J. G. *Arch. Biochem. Biophys.* 1967, 121, 619.
(20) Hassner, A.; Bimbaum, D.; Loew, L. M. *J. Org. Chem.* 1984, 49, 2546.
(21) Fromherz, P.; Röcker, C. *Ber. Bunsenges. Phys. Chem.* 1994, 98, 128.
(22) Gregoriadis, G. *Liposome Technology, Vol. 1, Preparation of Liposomes; CRC: Boca Raton,* 1984; Vol. 1.
(23) MacDonald, R. C.; MacDonald, R. I.; Menco, B. P. M.; Takeshita, K.; Subbarao, N. K.; Hu, L. R. *Biochim. Biophys. Acta* 1991, 1061, 297.
(24) Eriksson, H. J. C.; Somsen, G. W.; Hinrichs, W. L. J.; Frijink, H. W.; de Jong, G. J. *J. Chromatogr. B* 2001, 755, 311.
(25) Grit, M.; Crommelin, D. J. *Chem. Phys. Lipids* 1993, 64, 3.
(26) Buser, C. A.; McLaughlin, S. *Methods Mol. Biol.* 1998, 84, 267.
(27) Dimitrov, D. S.; Angelova, M. I. *Bioelectrochem. Bioenerg.* 1988, 253, 323.
(28) Fromherz, P.; Kiessling, V.; Kottig, K.; Zeck, G. *Appl. Phys. A* 1999, 69, 571.
(29) Schwoch, G.; Passow, H. *Mol. Cell. Biochem.* 1973, 2, 197.
(30) Ephardt, H.; Fromherz, P. *J. Phys. Chem.* 1989, 93, 7717.
(31) Heerklotz, H.; Seelig, J. *Biochim. Biophys. Acta* 2000, 1508, 69.
(32) Fromherz, P.; Schenk, O. *Biochim. Biophys. Acta* 1993, 1191, 299.
(33) Fernandez, M. S.; Fromherz, P. *J. Phys. Chem.* 1977, 81, 1755.
(34) Bom, M. Z. *Physik* 1920, 1, 45.
(35) Shannon, R. D. *Acta Crystallogr. A.* 1976, 32, 751.
(36) McLaughlin, S. *Curr. Top. Membr. Transp.* 1977, 9, 71.
(37) Tan, A.; Ziegler, A.; Steinbauer, B.; Seelig, J. *Biophys. J.* 2002, 83, 1547.
(38) Todd, M. J.; Gomez, J. *Anal. Biochem.* 2001, 296, 179.
(39) Tewari, Y. B.; Steckler, D. K.; Goldberg, R. N.; Gitomer, W. L. *J. Biol. Chem.* 1988, 263, 3670.
(40) Visser, N. V.; van Hoek, A.; Visser, A. J.; Frank, J.; Apell, H. J.; Clarke, R. J. *Biochemistry* 1995, 34, 11777.

The invention claimed is:

1. A method for the enzymatic activation of an amphiphilic voltage-sensitive dye comprising
   (a) providing a precursor to the amphiphilic voltage-sensitive dye with said precursor having an enzymatically cleavable hydrophilic group at a lipophilic tail of the amphiphilic voltage-sensitive dye,
   (b) cleaving the precursor to the amphiphilic voltage-sensitive dye using an enzyme expressed by a target cell, thereby forming the amphiphilic voltage-sensitive dye, and
   (c) binding the amphiphilic voltage-sensitive dye to a lipophilic interior of a lipid membrane of the target cell.

2. The method of claim 1, wherein the membrane is a lipid membrane of a nerve cell or a cancer cell.

3. The method according to claim 1, wherein a voltage-sensitive fluorescent dye is used.

4. The method according to claim 1, wherein the dye precursor is a voltage sensitive dye precursor of the formula (I)

wherein A denotes a voltage-sensitive chromophore which optionally can contain one or more groups Q selected from  —(CH$_2$)$_m$SO$_2$OH, —(CH$_2$)$_m$—N$^+$(CH$_3$)$_3$, —CH$_2$—CHOH—CH$_2$—N$^+$(CH$_3$)$_2$—CH$_2$—CH$_2$—OH, —OH, —O—PO(OH)$_2$, —O—SO$_2$OH, —(CH$_2$)$_n$—OH, —(CH$_2$)$_n$—O—PO(OH)$_2$, —(CH$_2$)$_n$—O—SO$_2$OH, an N- or O-linked (poly)carbohydrate and/or an N- or O-linked (poly)amino acid, X denotes a polar head group selected from —(CH$_2$)$_m$—SO$_2$OH, —(CH$_2$)$_m$—N$^+$(CH$_3$)$_3$, —CH$_2$—CHOH—CH$_2$—N$^+$(CH$_3$)$_2$—CH$_2$—CH$_2$—OH, m and n independently represent integers from 0 to 20 or X represents a group —R$^3$Y or a group Y, wherein R$^3$ is a hydrocarbon linking group with 1-20 C atoms and wherein Y is selected from —O—PO(OH)$_2$, —O—SO$_2$OH, an N- or O-linked (poly)carbohydrate and/or an N- or O-linked (poly)amino acid, Z is selected from N, P, As, Sb or Bi, and R$^1$ and R$^2$ independently at each occurrence represent a C$_1$-C$_{20}$ hydrocarbon residue which can be substituted by one or more groups Y, with the proviso that the dye precursor contains at least one group Y.

5. The method according to claim 4, wherein at least one residue R$^1$ and/or R$^2$ contains one or more groups Y.

6. The method according to claim 3, wherein the voltage-sensitivity and/or fluorescence of the dye is activated by cleaving the dye precursor.

7. A method for the enzymatic activation of an amphiphilic voltage-sensitive dye comprising
   (a) providing a precursor to the amphiphilic voltage-sensitive dye with said precursor having an enzymatically cleavable hydrophilic group at a lipophilic tail of the amphiphilic voltage-sensitive dye,
   (b) cleaving the precursor to the amphiphilic voltage-sensitive dye using an enzyme expressed by a target cell, thereby forming the amphiphilic voltage-sensitive dye, and
   (c) binding the amphiphilic voltage-sensitive dye to a lipophilic interior of a lipid membrane of the target cell, wherein the enzyme is overexpressed by a transfected cell and provided with a targeting signal which directs the enzyme to the cell wall.

8. A method for the enzymatic activation of an amphiphilic voltage-sensitive dye comprising
   (a) providing a precursor to the amphiphilic voltage-sensitive dye with said precursor having an enzymatically cleavable hydrophilic group at a lipophilic tail of the amphiphilic voltage-sensitive dye,
   (b) cleaving the precursor to the amphiphilic voltage-sensitive dye using an enzyme expressed by a target cell, thereby forming the amphiphilic voltage-sensitive dye, and
   (c) binding the amphiphilic voltage-sensitive dye to a lipophilic interior of a lipid membrane of the target cell, wherein dye not bound to the membrane is reconverted into the dye precursor by a second enzyme.

9. The method according to claim 1 for intracellular staining.

10. A voltage sensitive dye precursor having the formula (I)

$$X\text{-}A\text{-}Z\text{-}R^1R^2 \qquad (I)$$

wherein A denotes a voltage sensitive chromophore selected from

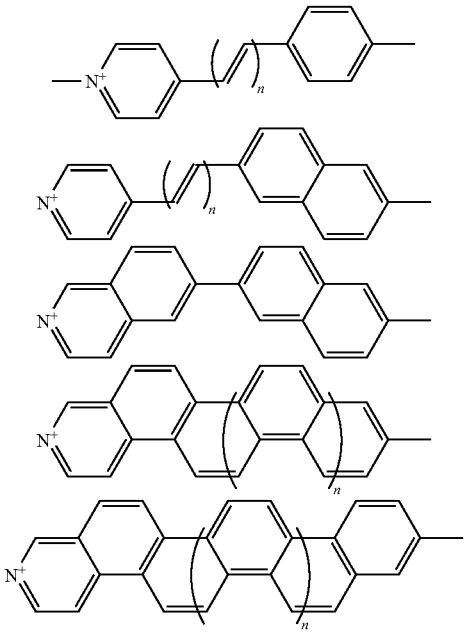

X denotes a polar head group selected from $-(CH_2)_m-SO_2H$, $-(CH_2)_m-N^+(CH_3)_3$ or $-CH_2-CHOH-CH_2-N^+(CH_3)_2-CH_2-CH_2-OH$, m is an integer from 0 to 6, Z is selected from N, P, As, Sb or Bi and $R^1$ and $R^2$ independently at each occurrence represent a $C_{10}$-$C_{20}$ hydrocarbon residue which is substituted with at least one group selected from a (poly-)phosphate group or a (poly-)carbohydrate group.

* * * * *